US008586015B2

(12) United States Patent
Panandiker et al.

(10) Patent No.: US 8,586,015 B2
(45) Date of Patent: Nov. 19, 2013

(54) COMPOSITIONS COMPRISING SURFACTANTS AND GLYCEROL-MODIFIED SILICONES

(75) Inventors: Rajan Keshav Panandiker, West Chester, OH (US); Steven Daryl Smith, Fairfield, OH (US); Bernard William Kluesener, Harrison, OH (US); Mark Gregory Solinsky, Cincinnati, OH (US); Matthew Scott Wagner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/078,167

(22) Filed: Apr. 1, 2011

(65) Prior Publication Data

US 2011/0243871 A1 Oct. 6, 2011

Related U.S. Application Data

(60) Provisional application No. 61/320,133, filed on Apr. 1, 2010, provisional application No. 61/320,141, filed on Apr. 1, 2010, provisional application No. 61/366,270, filed on Jul. 21, 2010, provisional application No. 61/383,770, filed on Sep. 17, 2010, provisional application No. 61/413,062, filed on Nov. 12, 2010.

(51) Int. Cl.
*A61Q 19/00* (2006.01)
*A61Q 5/00* (2006.01)
*A61Q 1/00* (2006.01)
*A61K 8/894* (2006.01)

(52) U.S. Cl.
USPC .................. 424/70.12; 424/70.19; 424/70.21; 424/70.22; 424/70.24; 424/70.27; 424/70.28; 424/70.31; 510/466; 556/450; 556/453

(58) Field of Classification Search
USPC .......... 424/70.12, 70.19, 70.21, 70.22, 70.24, 424/70.27, 70.28, 70.31; 510/466; 556/450, 556/453
See application file for complete search history.

(56) References Cited

U.S. PATENT DOCUMENTS 3,663,649 A 5/1972 Wheeler, Jr.
4,341,675 A 7/1982 Nakamura
4,680,366 A 7/1987 Tanaka et al.
4,939,007 A 7/1990 Hu et al.
5,025,076 A 6/1991 Tanaka et al.
5,063,051 A 11/1991 Grollier et al.
5,104,643 A 4/1992 Grollier et al.
5,144,054 A * 9/1992 Shioya et al. ................. 556/445
5,262,155 A * 11/1993 Vincent et al. ............. 424/78.02
5,282,871 A 2/1994 Yamane et al.
5,306,838 A * 4/1994 Shioya et al. ................. 556/445
5,346,642 A 9/1994 Patel et al.
5,466,849 A * 11/1995 Shioya et al. ................. 424/401
5,536,332 A 7/1996 Chun
5,540,853 A * 7/1996 Trinh et al. ................... 510/101
5,548,054 A * 8/1996 Okada et al. .................... 528/25
6,010,689 A * 1/2000 Matsumoto et al. ......... 424/70.1
6,171,515 B1 1/2001 Evans et al.
6,204,329 B1 3/2001 Leboucher et al.
6,340,662 B1 1/2002 Millhoff et al.
6,682,749 B1 1/2004 Potechin et al.
6,770,263 B1 * 8/2004 Brucker .......................... 424/45
7,074,419 B2 7/2006 Dietz et al.
7,153,922 B2 12/2006 Hohberg et al.
1,887,024 A1 12/2008 Ferenz et al.
7,608,575 B2 10/2009 Panandiker et al.
2004/0048996 A1 3/2004 Lange et al.
2004/0171759 A1 9/2004 Lange et al.
2004/0236055 A1 11/2004 Danner
2005/0187121 A1 8/2005 Dietz
2005/0255075 A1 11/2005 Meder et al.
2006/0052273 A1 3/2006 Terada
2006/0163524 A1 7/2006 Lange et al.
2007/0100107 A1 5/2007 Terry, Jr. et al.
2007/0190012 A1 8/2007 Feng et al.
2007/0225195 A1 9/2007 Saito et al.
2008/0209645 A1 9/2008 Carrillo et al.
2008/0234165 A1 * 9/2008 Panandiker et al. .......... 510/299
2008/0292560 A1 11/2008 Tamarkin et al.
2009/0068136 A1 * 3/2009 Beumer et al. ............. 424/70.16
2010/0247689 A1 9/2010 Paspaleeva-Kühn et al.
2011/0240065 A1 10/2011 Panandiker et al.
2011/0243874 A1 10/2011 Panandiker et al.

(Continued)

FOREIGN PATENT DOCUMENTS

DE 19957505 A1 3/2001
DE 10 2004 04423 A1 8/2005

(Continued)

OTHER PUBLICATIONS

Ikeda et al. (EP 1944330 B1 Date of Publication Jul. 16, 2008).*

(Continued)

*Primary Examiner* — Richard Schnizer
*Assistant Examiner* — Alma Pipic
(74) *Attorney, Agent, or Firm* — James F. McBride; Steven W. Miller

(57) ABSTRACT

The present application relates to organosilicones and compositions such as consumer products comprising such organosilicones, as well as processes for making and using such organosilicones and such compositions. Such compositions comprising such organosilicones are easier to formulate, and provide more economical and superior care benefits when compared to current silicone containing compositions.

11 Claims, 1 Drawing Sheet

(56) References Cited

U.S. PATENT DOCUMENTS

| | | | |
|---|---|---|---|
| 2011/0243875 A1 | 10/2011 | Panandiker et al. | |
| 2011/0243876 A1 | 10/2011 | Panandiker et al. | |
| 2011/0243878 A1 | 10/2011 | Panandiker et al. | |

FOREIGN PATENT DOCUMENTS

| | | | | |
|---|---|---|---|---|
| EP | 0 294 893 | A2 | | 12/1988 |
| GB | 602109 | A | | 5/1948 |
| JP | 4 011078 | A | | 1/1992 |
| JP | 05124936 | A | * | 5/1993 |
| JP | 6 184946 | A | | 7/1994 |
| JP | 9 194335 | A | | 7/1997 |
| JP | 2002 226321 | A | | 8/2002 |
| WO | WO 02/36873 | A2 | | 5/2002 |
| WO | WO 2005/123789 | A1 | | 12/2005 |
| WO | WO 2007/049188 | | * | 5/2007 |

OTHER PUBLICATIONS

Ayumi et al. (H8-217636 published 1995, machine translation appended thereto).*
All Office Actions, U.S. Appl. No. 13/078,079.
All Office Actions, U.S. Appl. No. 13/078,093.
All Office Actions, U.S. Appl. No. 13/078,114.
All Office Actions, U.S. Appl. No. 13/078,182.
All Office Actions, U.S. Appl. No. 13/078,103.
Pinteala, M. et al., Functional Polysiloxanes. 2. On the Reaction of Hydroxypropyl- and Aminoalkyl—Terminated Polydimethylsiloxanes With Cyclic Anydrides, Polymer Bulletin, Springer, Heidelberg, DE, vol. 32, No. 2, Feb. 1, 1994, pp. 173-178.
International Search Report; International Application No. PCT/US2011/030854; date of mailing Sep. 14, 2011; 6 pages.
International Search Report; International Application No. PCT/US2011/030857; date of mailing Jun. 29, 2011; 4 pages.
International Search Report; International Application No. PCT/US2011/030858; date of mailing May 27, 2011; 4 pages.
International Search Report; International Application No. PCT/US2011/030847; date of mailing Sep. 28, 2011; 4 pages.
International Search Report; International Application No. PCT/US2011/030852; date of mailing Jul. 5, 2011; 4 pages.
International Search Report; International Application No. PCT/US2011/030860; date of mailing Jul. 20, 2011; 4 pages.
All Office Actions, U.S. Appl. No. 13/249,831.
All Office Actions, U.S. Appl. No. 13/249,894.

* cited by examiner

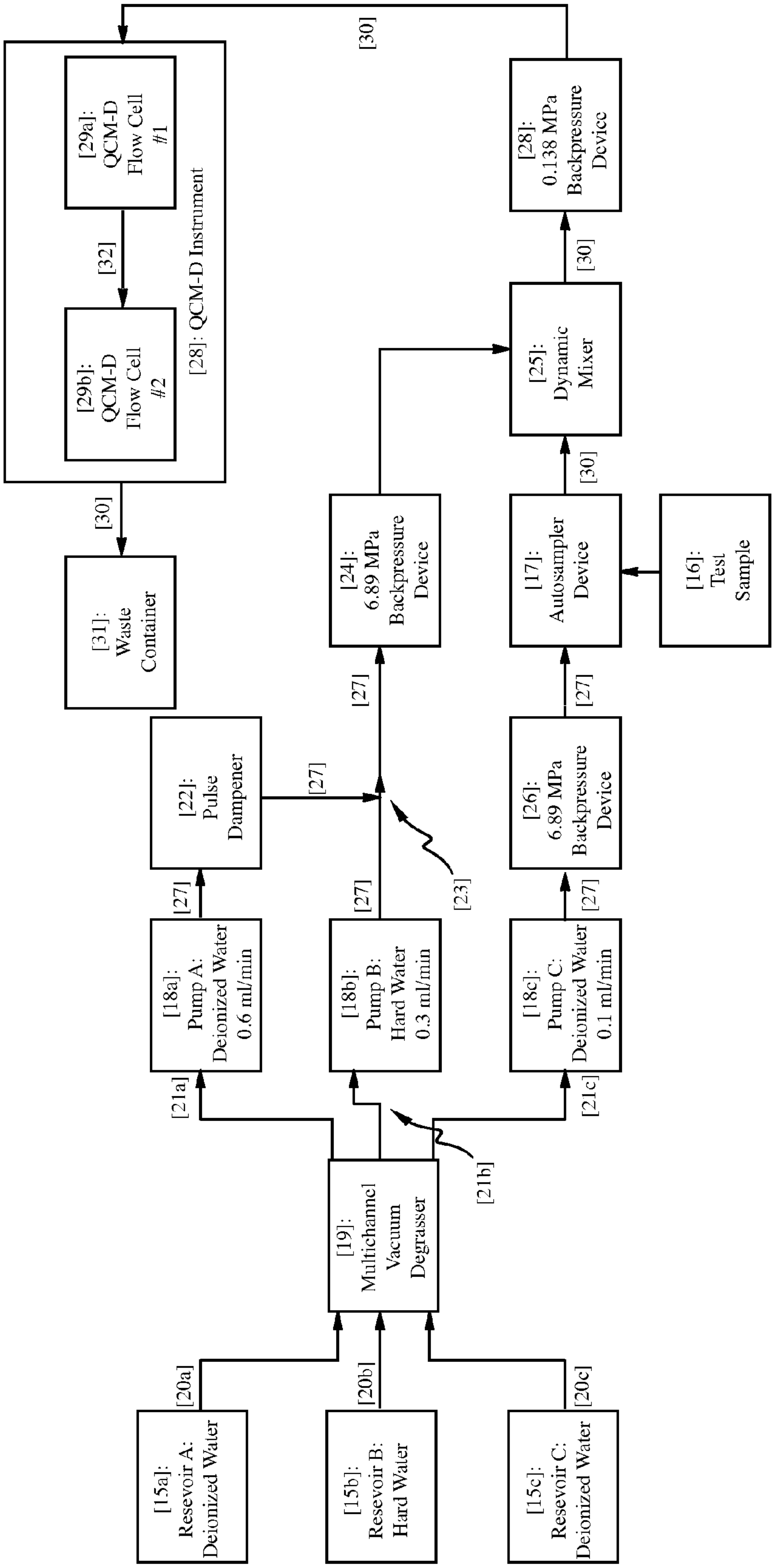
[15a]: Resevoir A: Deionized Water
[15b]: Resevoir B: Hard Water
[15c]: Resevoir C: Deionized Water
[20a]
[20b]
[20c]
[19]: Multichannel Vacuum Degrasser
[21a]
[21b]
[21c]
[18a]: Pump A: Deionized Water 0.6 ml/min
[18b]: Pump B: Hard Water 0.3 ml/min
[18c]: Pump C: Deionized Water 0.1 ml/min
[27]
[22]: Pulse Dampener
[23]
[26]: 6.89 MPa Backpressure Device
[24]: 6.89 MPa Backpressure Device
[17]: Autosampler Device
[16]: Test Sample
[25]: Dynamic Mixer
[30]
[28]: 0.138 MPa Backpressure Device
[29a]: QCM-D Flow Cell #1
[32]
[29b]: QCM-D Flow Cell #2
[28]: QCM-D Instrument
[31]: Waste Container

COMPOSITIONS COMPRISING SURFACTANTS AND GLYCEROL-MODIFIED SILICONES

CROSS-REFERENCES TO RELATED APPLICATIONS

This application claims priority under 35 U.S.C. §119(e) to U.S. Provisional Application Ser. No. 61/320,133 filed Apr. 1, 2010; U.S. Provisional Application Ser. No. 61/320,141 filed Apr. 1, 2010; U.S. Provisional Application Ser. No. 61/366,270 filed Jul. 21, 2010; U.S. Provisional Application Ser. No. 61/383,770 filed Sep. 17, 2010; and U.S. Provisional Application Ser. No. 61/413,062 filed Nov. 12, 2010.

FIELD OF INVENTION

The present application relates to organosilicones and compositions such as consumer products comprising such organosilicones, as well as processes for making and using such organosilicones and such compositions.

BACKGROUND OF THE INVENTION

Silicones are used in premium consumer products to benefits such as softness, hand, anti-wrinkle, hair conditioning/frizz control, color protection etc. Unfortunately, silicones, including current organosilicones, are expensive, difficult to process, and may lack the required chemical and/or physical stability. Typically, such physical and/or chemical stability problems manifest themselves as creaming and/or discoloration of a consumer product that comprises silicone. In addition, such discoloration may not only occur in product but also on surfaces that are treated with the consumer product that comprises the silicone. Current silicone technologies are expensive due to the cost of raw silicone raw materials and the silicone emulsification step that is required to make such silicones useful in products. Thus, what is needed is an economical silicone technology that has the required chemical and physical stability when used in a consumer product.

Fortunately, Applicants recognized that the source of the problem driving the need for the silicone emulsification step was the lack of functional groups on the silicone. Thus, Applicants discovered that certain low cost functional groups can be attached to a silicone to yield an organosilicone that can be easily emulsified and therefore economical silicone. In addition, Applicants realized that certain, select functional groups can provide dramatically higher care benefits than the general pool of functional groups.

Thus, Applicants disclose certain highly effective, economical organosilicones and compositions such as consumer products comprising such organosilicones, as well as processes for making and using such organosilicones and such compositions.

SUMMARY OF THE INVENTION

The present application relates to organosilicones and compositions such as consumer products comprising such organosilicones, as well as processes for making and using such organosilicones and such compositions.

BRIEF DESCRIPTION OF THE FIGURES

FIG. 1 is a schematic of a combined QCM-D and HPLC Pump set-up.

DETAILED DESCRIPTION OF THE INVENTION

Definitions

As used herein "consumer product" means baby care, beauty care, fabric & home care, family care, feminine care, health care, products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, and tooth whitening.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

As used herein the term "siloxyl residue" means a polydimethylsiloxane moiety. As used herein, "substituted" means that the organic composition or radical to which the term is applied is:

(a) made unsaturated by the elimination of elements or radical; or (b) at least one hydrogen in the compound or radical is replaced with a moiety containing one or more (i) carbon, (ii) oxygen, (iii) sulfur, (iv) nitrogen or (v) halogen atoms; or (c) both (a) and (b).

Moieties that may replace hydrogen as described in (b) immediately above, which contain only carbon and hydrogen atoms are all hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Specific non-limiting examples of such groups are:

$—CH_3$, $—CHCH_3CH_3$, $—(CH_2)_8CH_3$, $—CH_2—C\equiv CH$, $—CH=CH—CH=CH_2$, 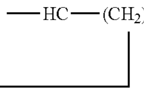

-φ$CH_3$, -φ$CH_2$φ, -φ, and -φ-φ.

Moieties containing oxygen atoms that may replace hydrogen as described in (b) immediately above include hydroxy, acyl or keto, ether, epoxy, carboxy, and ester containing groups. Specific non-limiting examples of such oxygen containing groups are:

$—CH_2OH$, $—CCH_3CH_3OH$, $—CH_2COOH$, $—C(O)—(CH_2)_8CH_3$, $—OCH_2CH_3$, $=O$, $—OH$, $—CH_2—O—CH_2CH_3$, $—CH_2—O—(CH_2)_2—OH$, $—CH_2CH_2COOH$, -φOH, -φ$OCH_2CH_3$, -φ$CH_2OH$,

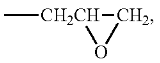 and 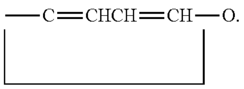

Moieties containing sulfur atoms that may replace hydrogen as described in (b) immediately above include the sulfur-containing acids and acid ester groups, thioether groups, mercapto groups and thioketo groups. Specific non-limiting examples of such sulfur containing groups are:

$—SCH_2CH_3$, $—CH_2S(CH_2)_4CH_3$, $—SO_3CH_2CH_3$, $SO_2CH_2CH_3$, $—CH_2COSH$, $—SH$, $—CH_2SCO$, $—CH_2C(S)CH_2CH_3$, $—SO_3H$, $—O(CH_2)_2C(S)CH_3$, $—S$, and 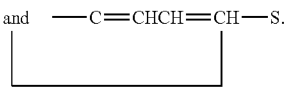

Moieties containing nitrogen atoms that may replace hydrogen as described in (b) immediately above include amino groups, the nitro group, azo groups, ammonium groups, amide groups, azido groups, isocyanate groups, cyano groups and nitrile groups. Specific non-limiting examples of such nitrogen containing groups are: $—NHCH_3$, $—NH_2$, $—NH_3^+$, $—CH_2CONH_2$, $—CH_2CON_3$, $—CH_2CH_2CH=NOH$, —CN, $—CH(CH_3)CH_2NCO$, $—CH_2NCO$, —Nφ, -φN=NφOH, and ≡N. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety. Specific non-limiting examples of such halogen containing groups are: $—(CH_2)_3COCl$, -φ$F_5$, —φCl, $—CF_3$, and $—CH_2$φBr.

It is understood that any of the above moieties that may replace hydrogen as described in (b) can be substituted into each other in either a monovalent substitution or by loss of hydrogen in a polyvalent substitution to form another monovalent moiety that can replace hydrogen in the organic compound or radical.

As used herein "φ" represents a phenyl ring.

As used herein, the nomenclature $SiO_{"n"/2}$ represents the ratio of oxygen and silicon atoms. For example, $SiO_{1/2}$ means that one oxygen is shared between two Si atoms Likewise $SiO_{2/2}$ means that two oxygen atoms are shared between two Si atoms and $SiO_{3/2}$ means that three oxygen atoms are shared are shared between two Si atoms.

As used herein random means that the $[(R_4Si(X—Z)O_{2/2}]$, $[R_4R_4SiO_{2/2}]$ and $[R_4SiO_{3/2}]$ units are randomly distributed throughout the polymer chain.

As used herein blocky means that multiple units of $[(R_4Si(X—Z)O_{2/2}]$, $[R_4R_4SiO_{2/2}]$ and $[R_4SiO_{3/2}]$ units are placed end to end throughout the polymer chain.

When a moiety or an indice of a preferred embodiment is not specifically defined, such moeity or indice is as previously defined.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Consumer Products Comprising Organosilicones

In a first aspect, a composition comprising, based on total composition weight:

a) from about 0.1% to about 50%, from about 0.5% to about 30% or even from about 1% to about 20% of a surfactant selected from the group consisting of anionic, cationic, amphoteric, zwitterionic, nonionic surfactants, and combinations thereof; and b) from about 0.01% to about 20%, from about 0.1% to about 10% or even from about 0.2% to about 8% an organosilicone polymer selected from the group consisting of a random or blocky organosiloxane having the structure $$[R_1R_2R_3SiO_{1/2}]_{(j+2)}[(R_4Si(X—Z)O_{2/2}]_k[R_4R_4SiO_{2/2}]_m[R_4SiO_{3/2}]_j$$

wherein j is an integer from 0 to about 98; in one aspect j is an integer from 0 to about 48; in one aspect, j is 0;

k is an integer from 0 to about 200; when k=0, at least one of $R_1$, $R_2$ or $R_3$=—X—Z, in one aspect, k is an integer from 0 to about 50 m is an integer from 4 to about 5,000; in one aspect m is an integer from about 10 to about 4,000; in another aspect m is an integer from about 50 to about 2,000;

$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—Z;

each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;

each X comprises of a divalent alkylene radical comprising 2-12 carbon atoms; in one aspect each X is independently selected from the group consisting of —$(CH_2)_s$—O—; —$(CH_2)_s$—O—$(CHR_6$—$CHR_6)_w$—O; —$CH_2$—CH(OH)—$CH_2$—O—;

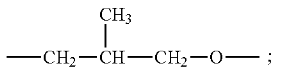

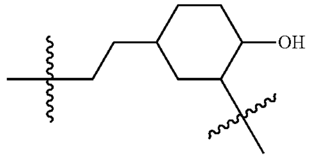

and

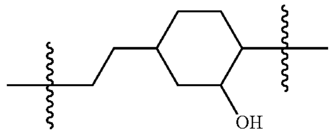

wherein each s independently is an integer from about 2 to about 8, in one aspect s is an integer from about 2 to about 4;

At least one Z in the said organosiloxane is selected from the group consisting of $R_5$;

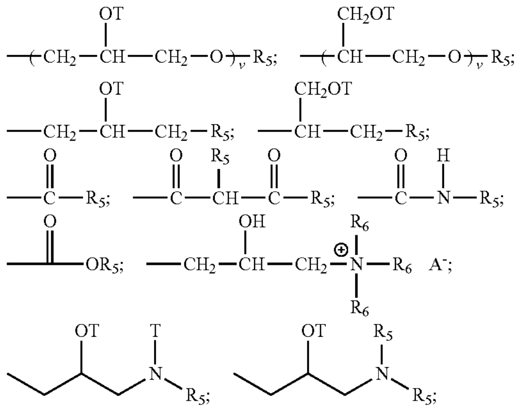

—$C(R_5)_2O$—$R_5$; —$C(R_5)_2S$—$R_5$ and

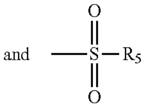

provided that when X is

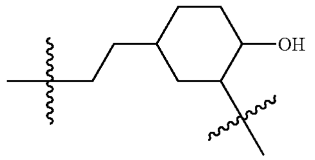

or

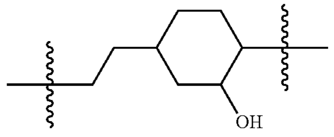

then Z=—$OR_5$ or

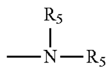

wherein $A^-$ is a suitable charge balancing anion. In one aspect $A^-$ is selected from the group consisting of $Cl^-$, $Br^-$, $I^-$, methylsulfate, toluene sulfonate, carboxylate and phosphate and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $R_5$,

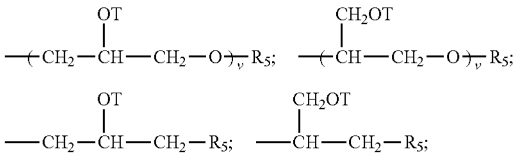

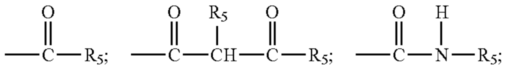

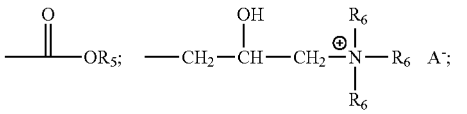

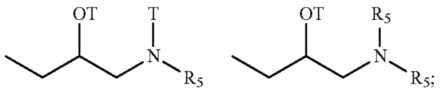

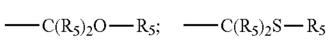

and

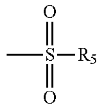

provided that when X is

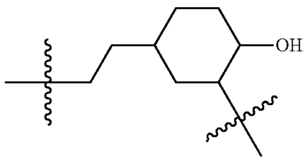

or

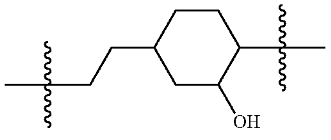

then Z=—$OR_5$ or

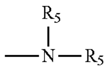

each $R_5$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl or $C_6$-$C_{32}$ alkylaryl, or $C_6$-$C_{32}$ substituted alkylaryl, —$(CHR_6$—$CHR_6$—O—$)_w$—$CHR_6$—$CHR_6$-L and siloxyl residue wherein each L is independently selected from —O—C(O)—$R_7$ or —O—$R_7$;

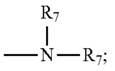

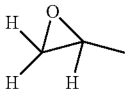

and

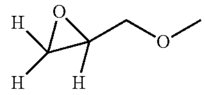

w is an integer from 0 to about 500, in one aspect w is an integer from 0 to about 200, one aspect w is an integer from 0 to about 50;

each $R_6$ is independently selected from H or $C_1$-$C_{18}$ alkyl;

each $R_7$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted aryl, and a siloxyl residue;

each T is independently selected from H;

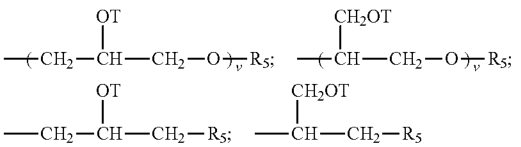

wherein each v in said organosilicone is an integer from 1 to about 10, in one aspect, v is an integer from 1 to about 5 and the sum of all v indices in each Z in the said organosilicone is an integer from 1 to about 30 or from 1 to about 20 or even from 1 to about 10;

is disclosed

In a second aspect of such composition, the organosilicone polymer may be defined by the following formula $$[R_1R_2R_3SiO_{1/2}]_{(j+2)}[R_4R_4SiO_{2/2}]_m[R_4SiO_{3/2}]_j$$

$R_1$ and $R_2$ are each independently selected from the group consisting of H, OH, $C_1$-$C_{32}$ alkyl, in one aspect methyl, and $C_1$-$C_{32}$ alkoxy, in one aspect —$OCH_3$ or —$OC_2H_5$; and $R_3$ is —X—Z, j is an integer selected from 0 to about 48, and all other indices and moieties are as described in such first aspect.

In a third aspect, of such composition said organosilicone polymer may have a structure selected from:

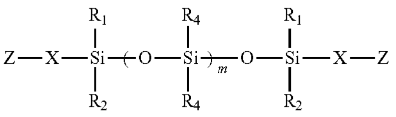

$R_1$ and $R_2$ are each independently selected from $C_1$-$C_{32}$ alkyl and $C_1$-$C_{32}$ alkoxy; and all other indices and moieties are as described in said first and second aspects.

In a fourth aspect, at least one Z in said organosilicone polymer is independently selected from the group consisting of —$CH_2$—CH(OH)—$CH_2$—$R_5$;

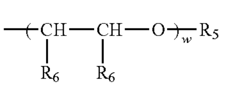

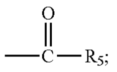

-continued

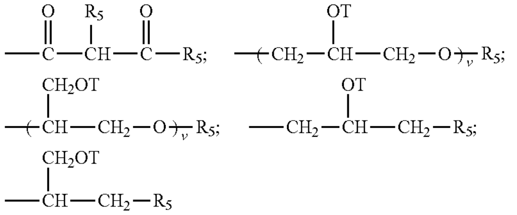

and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl; —$CH_2$—CH(OH)—$CH_2$—$R_5$;

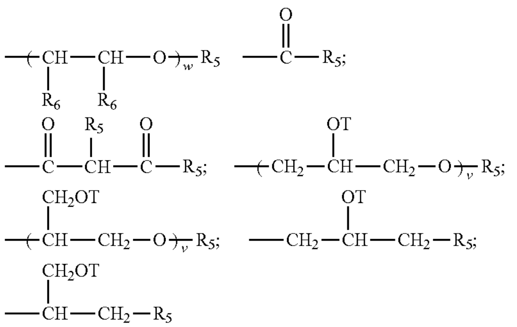

and all other indices and moieties are as described in aspect 3.

In a fifth aspect, the organosilicone polymer defined by the following formula $$[R_1R_2R_3SiO_{1/2}]_{(j+2)}[(R_4Si(X—Z)O_{2/2}]_k[R_4R_4SiO_{2/2}]_m[R_4SiO_{3/2}]_j$$

wherein $R_1$ and $R_2$ and $R_3$ are selected from the group consisting of H; —OH; $C_1$-$C_{32}$ alkyl, in one aspect, methyl, and $C_1$-$C_{32}$ alkoxy; and k is an integer from 1 to about 50, j is an integer form 0 to 48 and all other indices and moieties are as defined in said first aspect.

In a sixth aspect, a said organosilicone polymer has a structure selected from:

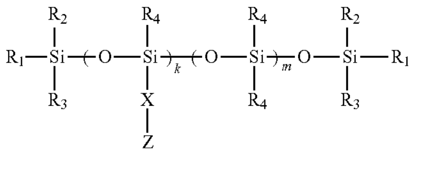

wherein least one Z in said organosilicone polymer is independently selected from the group consisting of —$CH_2$—CH(OH)—$CH_2$—$R_5$;

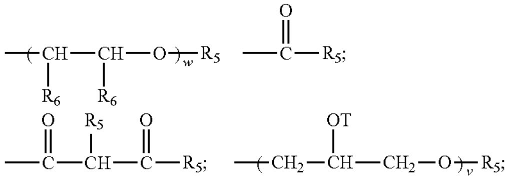

-continued

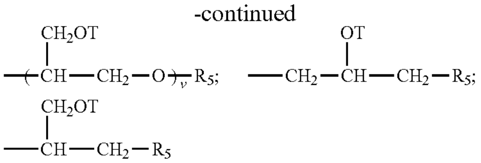

and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl; —$CH_2$—CH(OH)—$CH_2$—$R_5$;

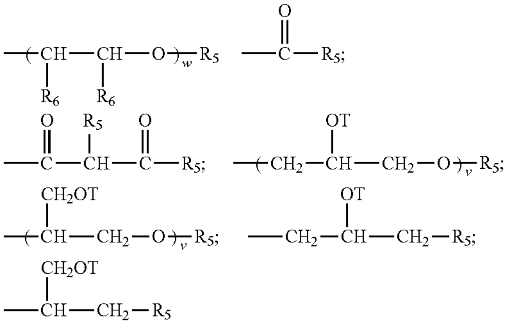

and all other indices and moieties are as described in said fifth aspect.

In a seventh aspect, the organosilicone polymer may be defined by the following formula $$[R_1R_2R_3SiO_{1/2}]_{(j+2)}[(R_4Si(X—Z)O_{2/2}]_k[R_4R_4SiO_{2/2}]_m[R_4SiO_{3/2}]_j,$$

wherein $R_1$, $R_2$ and $R_3$ are selected from the group consisting of H; —OH; $C_1$-$C_{32}$ alkyl, in one aspect methyl, and $C_1$-$C_{32}$ alkoxy in one aspect —$OCH_3$ or —$OC_2H_5$ and k is an integer selected from 1 to about 50 and j is an integer from 0 to about 48 and all other indices and moieties are as described in said first aspect.

In an eighth aspect, X is independently selected from the group consisting of —$(CH_2)_s$—O—; —$(CH_2)_s$—O—$(CHR_6$—$CHR_6)_w$—O; —$CH_2$—CH(OH)—$CH_2$—O—;

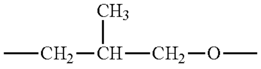

and at least one Z in the said organosiloxane is selected from the group consisting of

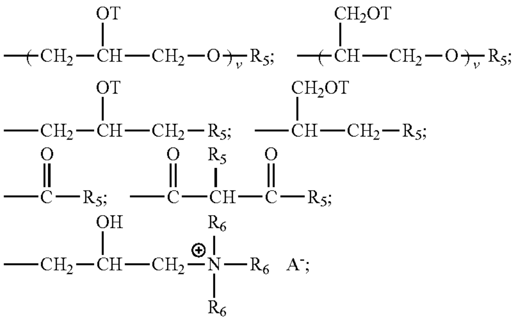

-continued

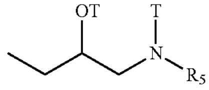

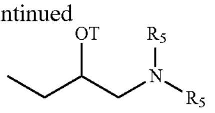

and each additional Z in said organosilicone is independently selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl;

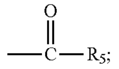

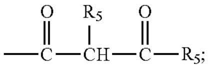

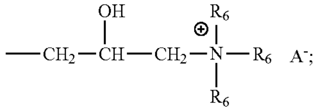

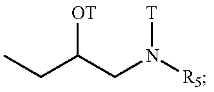

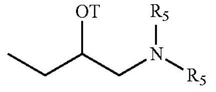

and all other indices and moieties are as defined in said seventh aspect.

In a ninth aspect, $R_1$ is —X—Z and $R_2$ and $R_3$ are selected from the group consisting of H; —OH; $C_1$-$C_{32}$ alkyl, in one aspect, methyl, and $C_1$-$C_{32}$ alkoxy, and k=0, j is an integer selected from 0 to about 48, X is independently selected from the group consisting of $—(CH_2)_s—O—$; $—(CH_2)_s—O—(CHR_6—CHR_6)_wO$; $—CH_2—CH(OH)—CH_2—O—$;

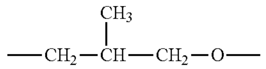

and at least one Z in the said organosiloxane is selected from the group consisting of

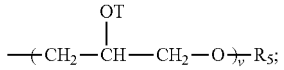

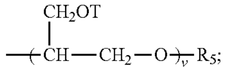

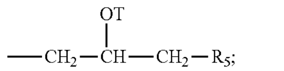

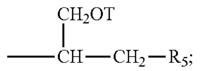

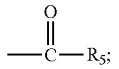

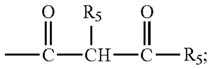

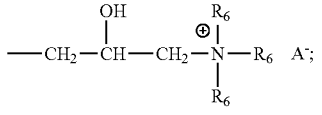

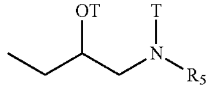

and

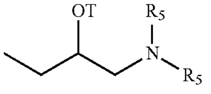

and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl,

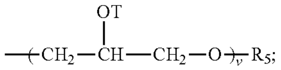

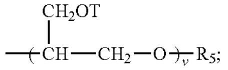

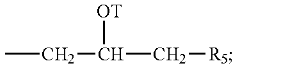

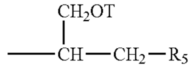

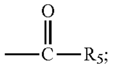

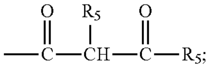

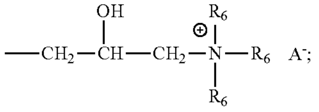

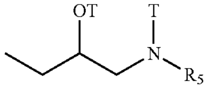

and

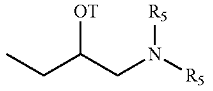

and all other indices and moieties are as defined in said first aspect.

In any of the aforementioned aspects, said composition may comprise a material selected from a perfume, a perfume delivery system, brightener, enzyme, deposition aid, structurant, surfactant, fabric softener active, and mixtures thereof.

In any of the aforementioned aspects, said composition may comprise an anionic surfactant.

Yet another aspect of the invention provides for a method of identifying a silicone emulsion for use as a fabric care active comprising the step of identifying the silicone emulsion's Tau Value. Having the desired Tau Value can result in a product having the correct feel benefit. In one aspect of the aforementioned compositions, the composition comprises an organosilicone polymer, when in the form of an emulsion, has a Tau Value of about 10 or less, below 10, below 8, below 5 or even from below 5 to about 0.5.

In one aspect, the aforementioned compositions are consumer products, for example cleaning and/or treatment compositions or even fabric and/or hard surface cleaning and/or treatment compositions. Additional descriptions of such products can be found, for example, in the present specification's sections titled "Personal Care Compositions", "Fabric and/or Hard Surface Cleaning and/or Treatment Compositions" and in this specification's examples.

Organosilicone and Processes of Making Same:

Suitable organosilicone polymers for use in the compositions disclosed herein also include organosilicone polymers that, in a first aspect, are selected from the group consisting of a random or blocky organosiloxane having the structure:

$$[R_1R_2R_3SiO_{1/2}]_{(j+2)}[(R_4Si(X—Z)O_{2/2}]_k[R_4R_4SiO_{2/2}]_m[R_4SiO_{3/2}]_j$$

wherein

- j is an integer from 0 to about 98; in one aspect j is an integer from 0 to about 48; in one aspect, j is 0;
- k is an integer from 0 to about 200; when k=0, at least one of $R_1$, $R_2$ or $R_3$ is —X—Z, in one aspect, k is an integer from 0 to about 50
- m is an integer from 4 to about 5,000; in one aspect m is an integer from about 10 to about 4,000; in another aspect m is an integer from about 50 to about 2,000;
- $R_1$, $R_2$, $R_3$ and $R_4$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy $C_1$-$C_{32}$ substituted alkoxy;

each X comprises of a divalent alkylene radical comprising 2-12 carbon atoms; in one aspect each X is independently selected from the group consisting of $-(CH_2)_s-O-$; $-(CH_2)_s-O-(CHR_6-CHR_6)_wO$; $-CH_2-CH(OH)-CH_2-O-$;

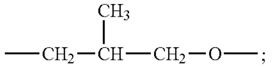

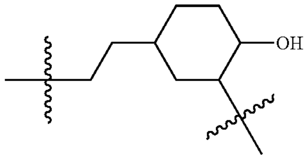

and

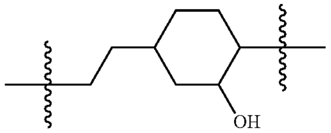

wherein each s independently is an integer from about 2 to about 8, in one aspect s is an integer from about 2 to about 4;

At least one Z in the said organosiloxane is selected from the group consisting of $R_5$;

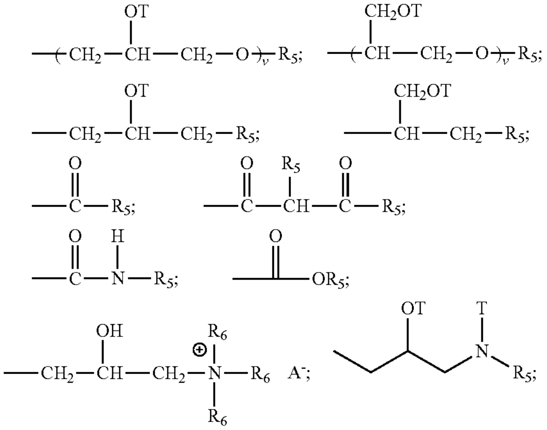

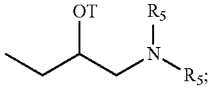

$-C(R_5)_2O-R_5$;

$-C(R_5)_2S-R_5$ and

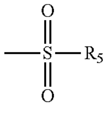

provided that when X is;

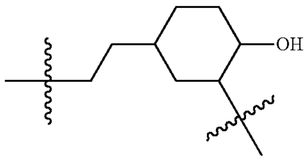

or

-continued

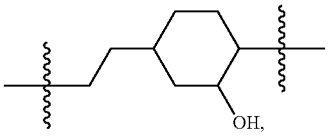

then $Z=-OR_5$ or

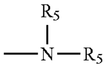

wherein $A^-$ is a suitable charge balancing anion. In one aspect $A^-$ is selected from the group consisting of $Cl^-$, $Br^-$, $I^-$, methylsulfate, toluene sulfonate, carboxylate and phosphate and each additional Z comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl; $R_5$;

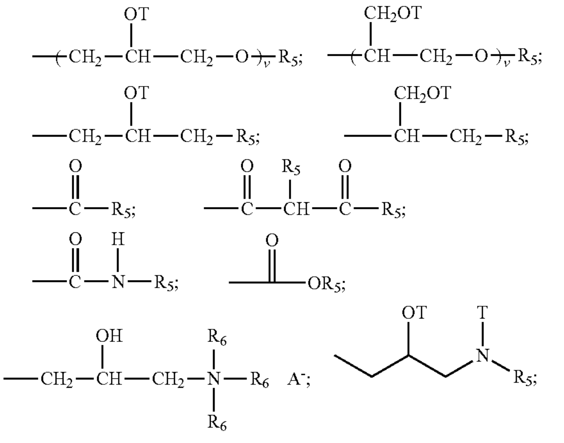

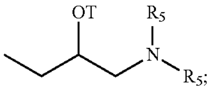

$-C(R_5)_2O-R_5$;

$-C(R_5)_2S-R_5$ and

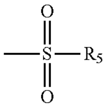

provided that when X is

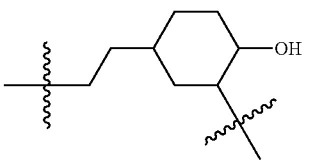

or

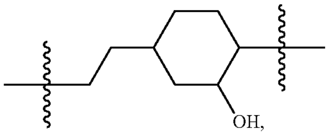

then Z=—$OR_5$ or

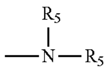

each $R_5$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl or $C_6$-$C_{32}$ substituted alkylaryl;

—$(CHR_6$—$CHR_6$—O—$)_w$—$CHR_6$—$CHR_6$-L, and a siloxyl residue, wherein each L is independently selected from —O—C(O)—$R_7$ or —O—$R_7$;

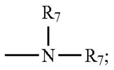

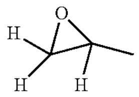

and

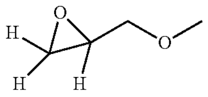

w is an integer from 0 to about 500, in one aspect w is an integer from 0 to about 200; in one aspect w is an integer from about 1 to about 50 each $R_6$ is independently selected from H or $C_1$-$C_6$ alkyl;

each $R_7$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl and a siloxyl residue each T is independently selected from H;

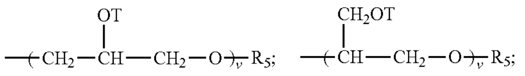

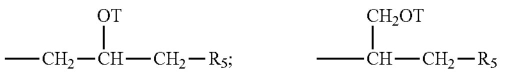

and wherein each v in said organosilicone is an integer from 1 to about 10. In one aspect v is an integer from 1 to about 5 and the sum of all v indices in each Z in the said organosilicone is an integer from 1 to about 30 or from 1 to about 20 or even from 1 to about 10.

In one aspect, suitable organosilicones are pendant organosilicones having the structure $$[R_1R_2R_3SiO_{1/2}]_{(j+2)}[(R_4Si(X—Z)O_{2/2}]_k[R_4R_4SiO_{2/2}]_m[R_4SiO_{3/2}]_j,$$

wherein $R_1$, $R_2$ and $R_3$ are selected from the group consisting of H; —OH; $C_1$-$C_{32}$ alkyl, in one aspect, methyl, and $C_1$-$C_{32}$ alkoxy, in one aspect, —$OCH_3$ or —$OC_2H_5$; and k is an integer from 1 to about 50 and j is an integer from 0 to about 48 with all other indices and moieties as previously defined in said first aspect.

In another aspect, a suitable organosiloxane may have the structure

Structure A

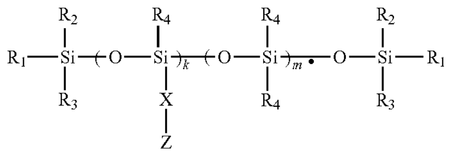

wherein $R_1$, $R_2$ and $R_3$ are selected from the group consisting of H; —OH; $C_1$-$C_{32}$ alkyl, and $C_1$-$C_{32}$ alkoxy and k is an integer from 1 to about 50 and j is an integer from 0 to about 48; X is independently selected from the group consisting of —$(CH_2)_s$—O—; —$(CH_2)_s$—O—$(CHR_6$—$CHR_6)_w$—O; —$CH_2$—CH(OH)—$CH_2$—O—;

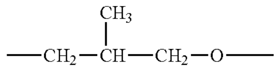

and at least one Z in the said organosiloxane is selected from the group consisting of

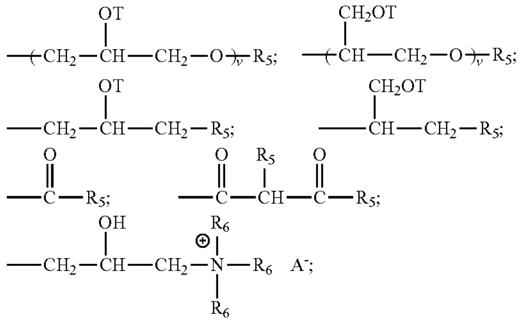

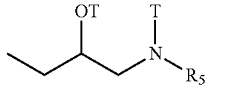

and

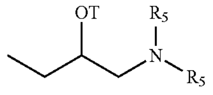

and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl;

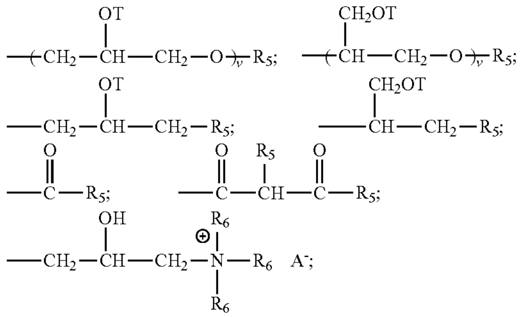

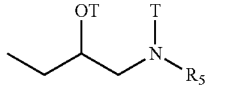

and

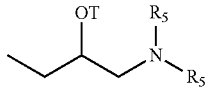

with all other indices and moieties as previously defined in said first aspect.

Organosilicones of Structure A are produced by reacting siloxane copolymers with pendant epoxy groups of the structure:

Structure B

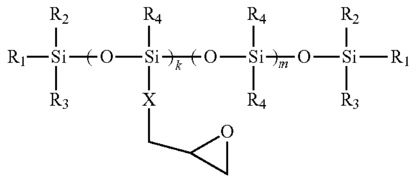

with a poly(oxyalkylene) with the structure

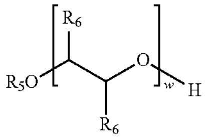

to produce the organosilicone

Structure C

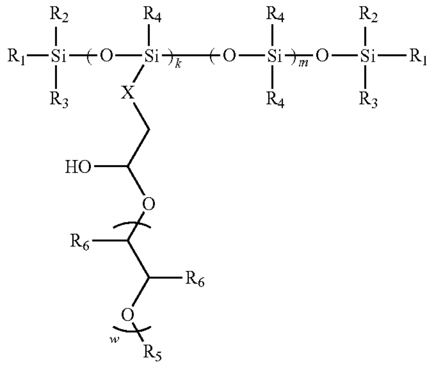

Wherein all indices and moieties of such reactants and Structure C are as previously defined in said first aspect.

It is recognized that any non-alkylated hydroxyl group, including one from a poly(oxyalkylene) previously covalently bonded with the epoxy functionalized polysiloxane, can react with another epoxy group on the same polysiloxane chain or another copolymer, thus producing a crosslinked and/or branched organosiloxane.

Organosilicones of Structure A are also produced by reacting siloxane copolymers with pendant epoxy groups with the structure:

Structure D

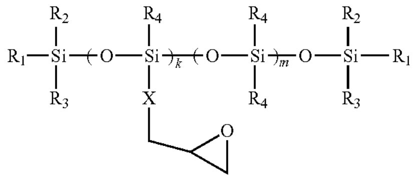

with a diamine that may have the structure

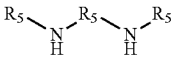

or in one aspect, the structure to produce the organosilicone

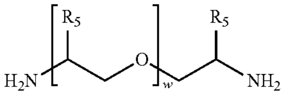

Structure E

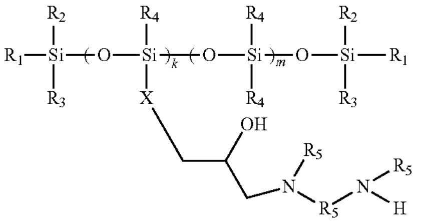

Wherein all indices and moieties of such reactants and Structure E are as previously defined in said first aspect.

It is recognized that any non-alkylated primary or secondary amine, including a diamine previously covalently bonded with the epoxy functionalized siloxane, or any non-alkylated hydroxyl group, can react with another epoxy group on the same siloxane chain or another epoxy functionalized siloxane thus producing a crosslinked and/or branched organosiloxane polymer.

Organosilicones of Structure A are also produced by reacting carbinol functional siloxane of the structure:

Structure F

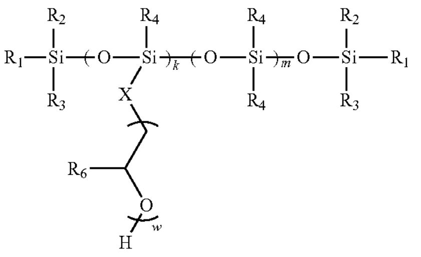

with a epoxide with the structure

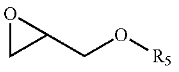

to produce the organosilicone

Structure G

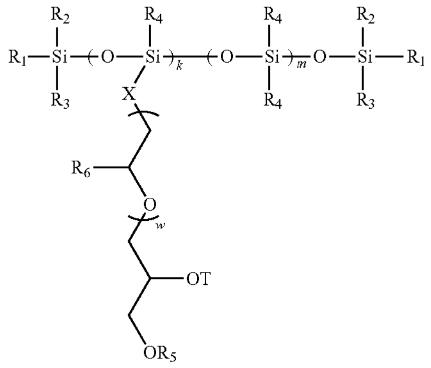

Wherein all indices and moieties of such reactants and Structure G are as previously defined in said first aspect.

It is also recognized that any non-ring opened epoxy or glycidyl ether group, especially one from a diepoxy structure previously covalently bonded with the carbinol functionalized siloxane, can react with another carbinol group on the same siloxane chain or another carbinol functional siloxane molecule, thus producing a crosslinked and/or branched organosilicone.

Another group of suitable organosiloxanes are linear organosiloxanes of the structure $$[R_1R_2R_3SiO_{1/2}]_{(j+2)}[R_4R_4SiO_{2/2}]_m[R_4SiO_{3/2}]_j$$

wherein j is an integer selected from 0 to about 48, $R_2$, $R_3$ and $R_4$ are each independently selected from the group consisting of H, OH, $C_1$-$C_{32}$ alkyl, in one aspect, methyl, and $C_1$-$C_{32}$ alkoxy X is independently selected from the group consisting of $—(CH_2)_s—O—$; $—(CH_2)_s—O—(CHR_6—CHR_6)_w—O$; $—CH_2—CH(OH)—CH_2—O—$;

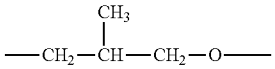

and at least one Z in the said organosiloxane is selected from the group consisting of

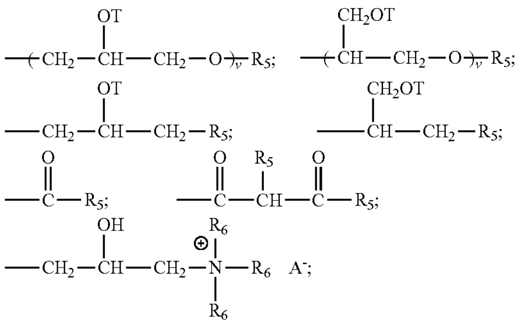

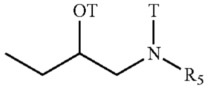

and

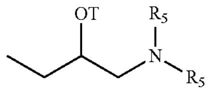

and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl,

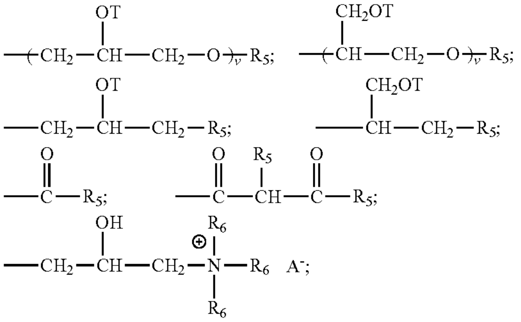

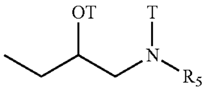

and

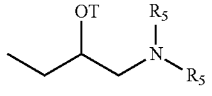

Wherein all indices and moieties of such reactants that are not defined are as previously defined in said first aspect.

Particularly suitable within this group are linear organosiloxanes of the structure:

Structure H

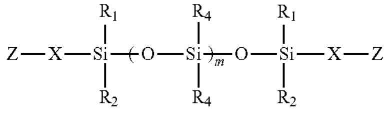

X is independently selected from the group consisting of $—(CH_2)_s—O—$; $—(CH_2)_s—O—(CHR_6—CHR_6)_wO$; $—CH_2—CH(OH)—CH_2—O—$;

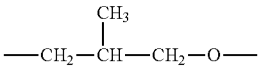

and at least one Z in the said organosiloxane is selected from the group consisting of

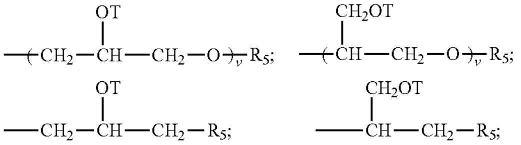

and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl,

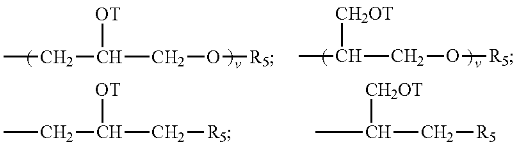

Wherein all indices and moieties of such structures that are not defined are as previously defined in said first aspect.

Organosilicones of this class are produced by reacting an epoxy terminated polysiloxane with a poly(oxyalkylene) with the structure

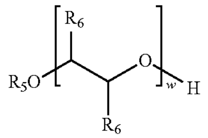

to produce the organosilicone of the structure epoxide is selected from the group consisting of diglycidyl ether terminated poly(dimethylsiloxane), epoxypropoxypropyl methylsiloxane-dimethylsiloxane copolymer and mixtures thereof; in one aspect, said organic compound comprises 1 to 4 hydroxyl groups, in one aspect said organic compound comprises 1 to 2 hydroxyl groups with a catalyst, to form a first mixture; or (ii) a carbinol functionalized siloxane copolymer and an organic compound comprising an epoxide group, in one aspect said carbinol functionalized siloxane copolymer comprises hydroxypropyleneoxypropylmethylsiloxane-dimethylsiloxane copolymer;

Structure I

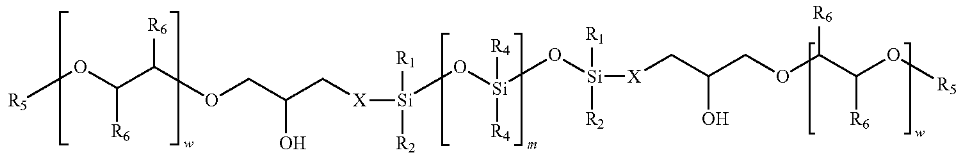

It is recognized that the epoxide can react with one or more of the resulting hydroxyl groups in the organosilicone to also produce branched structures and/or crosslinked structures.

Organosilicones of Structure K are produced by reacting a carbinol terminated polysiloxane of the structure:

Structure J

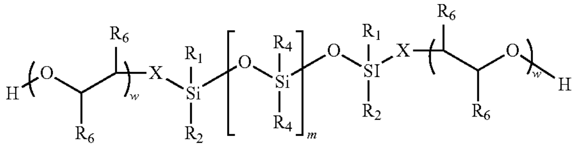

with an epoxide with the structure

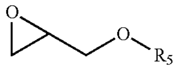

to produce the organosilicone b) heating said first mixture to a temperature of from about 20° C. to about 200° C., from about 20° C. to about 150° C., from about 20° C. to about 100° C., from about 30° C. to about 80° C., or even from about 40° C. to about 60° C., and maintaining said temperature for a time of from about 1 hours to about 48 hours, from about 2 hours to about 10 hours, to form a organo modified silicone that may optionally comprise impurities; and c) optionally purifying said first mixture, in one aspect, said purification comprises extraction with a fluid that said organo modified silicone is essentially insoluble, in one aspect, said soluble of said organo modified silicone in said solvent is less 10 grams of organo modified silicone per liter of solvent, in one aspect, said solvent comprises a material selected from the group consisting of water, methanol and mixtures thereof is disclosed.

In one aspect, a catalyst may be combined with the carbinol and the epoxide or silicone epoxide and hydroxyl group, the catalyst being used to react the epoxide with the carbinol or the silicone epoxide and hydroxyl group. This reaction may optionally take place in a solvent. Suitable solvents include any solvent that is not reactive to the epoxide and that solubilizes the reagents, e.g., toluene, dichloromethane, tetrahy- Structure K

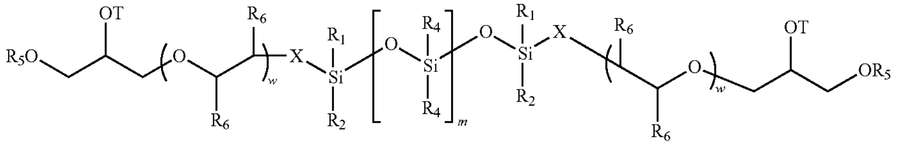

It is recognized that the epoxide can react with one or more of the resulting hydroxyl groups in the organosilicone to also produce branched structures. Wherein all indices and moieties of such reactants and Structures are as previously defined in said first aspect.

In one aspect, process of making an organomodified silicone comprising:

a) combining (i) a silicone epoxide and an organic compound comprising an hydroxyl group, in one aspect, said silicone drofuran (THF). For example, a carbinol may be combined with an epoxide to form a first mixture. The first mixture may then be dissolved in toluene and a catalyst may be added to the mixture dissolved in toluene.

Suitable catalysts for making the organosilicones include, but are not limited to, metallic catalysts. The term "metallic catalyst" includes within its definition catalysts which include a metallic component. This definition includes metallic salts and materials such as $AlCl_3$, covalent compounds, and materials such as $BF_3$ and $SnCl_4$, all of which include a metallic component. The metallic component includes all elements commonly known as metals, such as alkali metals, alkaline earth metals, transition metals, and boron.

Suitable catalysts include, but are not limited to, $TiCl_4$, $Ti(OiPr)_4$, $ZnCl_2$, $SnCl_4$, $SnCl_2$, $FeCl_3$, $AlCl_3$, $BF_3$, platinum dichloride, copper(II) chloride, phosphorous pentachloride, phosphorous trichloride, cobalt(II) chloride, zinc oxide, iron (II) chloride and $BF_3$—$OEt_2$ and mixtures thereof. In some aspects, the metallic catalysts are Lewis acids. The metallic components of these Lewis acid catalysts include Ti, Zn, Fe, Sn, B, and Al. Suitable Lewis acid catalysts include $TiCl_4$, $SnCl_4$, $BF_3$, $AlCl_3$, and mixtures thereof. In some aspects, the catalyst is $SnCl_4$ or $TiCl_4$. The metallic Lewis acid catalysts may be employed at concentrations of about 0.1 mol % to about 5.0 mol %, in some aspects, about 0.2 mol % to about 1.0 mol %, in some aspects about 0.25 mol %.

Other suitable catalysts for making the organosilicones include basic or alkaline catalysts. The term "basic catalyst" includes within its definition catalysts which are basic or alkaline. This definition includes alkaline salts and materials such as KH, KOH, KOtBu, NaOEt, covalent compounds, and elements, such as metallic sodium.

Suitable catalysts include alkali metal alkoxylates, such as KOtBu, NaOEt, KOEt, NaOMe and mixtures thereof, NaH, NaOH, KOH, CaO, CaH, $Ca(OH)_2$, $Ca(OCH(CH_3)_2)_2$, Na and mixtures thereof. In some aspects, the catalyst is selected from alkali metal alkoxylates. In some aspects, the basic catalyst is a Lewis base. Suitable Lewis base catalysts include KOH, $NaOCH_3$, $NaOC_2H_5$, KOtBu, NaOH, and mixtures thereof. The Lewis base catalysts may be employed at concentrations of about 0.1 mol % to about 5.0 mol %, in some aspects, about 0.2 mol % to about 1.0 mol %. The alkali metal alkoxylate catalysts may be employed at concentrations of about 2.0 mol % to about 20.0 mol %, in some aspects, about 5.0 mol % to about 15.0 mol %.

Additionally, protic solvents may be used as a catalytic solvent in the reaction. Protic solvents are solvents that have a hydrogen atom bonded to an electronegative atom, yielding highly polarized bonds in which the hydrogen has proton-like character and can have hydrogen bonding characteristics. Examples of protic solvents suitable for use include but are not limited to the following: water, formic acid, ethylene glycol, methanol, 2,2,2-trifluoroethanol, ethanol, ammonia, isopropanol, acetic acid, diethyl amine, propanoic acid, n-propanol, n-butanol, and tert-butyl alcohol.

Disposable Treatment Articles

The Disposable Treatment Articles (DTA) may be any suitable wet-laid or air-laid, through-air-dried (TAD) or conventionally dried, creped or uncreped, meltblown or spundbond fibrous structure. In one example, the fibrous structures of the present invention are disposable. For example, the fibrous structures of the present invention are non-textile fibrous structures. In another example, the fibrous structures of the present invention are flushable, such as toilet tissue. The fibrous structures of the present invention may be employed in single or multi-ply sanitary tissue products, such as paper towels, toilet tissue, facial tissue and/or wipes.

Non-limiting examples of processes for making fibrous structures include known wet-laid papermaking processes and air-laid papermaking processes. Such processes typically include the steps of preparing a fibrous element composition, such as a fiber composition, in the form of a suspension in a medium, either wet, more specifically an aqueous medium, i.e., water, or dry, more specifically a gaseous medium, i.e. air. The suspension of fibers within an aqueous medium is oftentimes referred to as a fiber slurry. The fibrous element suspension is then used to deposit a plurality of fibrous elements onto a forming wire or belt, in the case of a wet-laid process, and a collection device or belt, in the case of an air-laid process. Further processing of the fibrous structure may be carried out such that a finished fibrous structure is formed. For example, in typical papermaking processes, the finished fibrous structure is the fibrous structure that is wound on the reel at the end of papermaking. The finished fibrous structure may subsequently be converted into a finished product, e.g. a sanitary tissue product. The fibrous structure may be subjected to a one or more converting operations, such as embossing, tuft-generating, thermal bonding and calendering. The random or blocky organosilicone polymers disclosed in the present specification may be deposited onto the fibrous structure at any process during the making and/or converting of the fibrous structure. In addition, the random or blocky organosilicone polymers disclosed in the present specification may be included in the fibrous slurry used to form the fibrous structure. In another example, the random or blocky organosilicone polymers disclosed in the present specification may be included in a surface treating composition, such as a surface softening composition and/or a lotion composition that is applied to a surface of the fibrous structure and/or by way of transfer from a drying belt and/or Yankee dryer during the fibrous structure making process. In yet another example, the random or blocky organosilicone polymers disclosed in the present specification may be printed onto a surface of the fibrous structure, such as via a gravure roll. The random or blocky organosilicone polymers disclosed in the present specification may also be sprayed onto a surface of the fibrous structure, such as by an ink-jet printing process. Lastly, the random or blocky organosilicone polymers disclosed in the present specification may be extruded onto a surface of the fibrous structure.

The fibrous structure may be made up of fibers and/or filaments. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

The fibers may be naturally occurring fibers, which means they are obtained from a naturally occurring source, such as a vegetative source, for example trees and/or plants. Such fibers are typically used in papermaking and are oftentimes referred to as papermaking fibers. Papermaking fibers useful in the present invention include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. Also applicable to the DTAs of the present invention are fibers derived from recycled paper.

In addition to the various wood pulp fibers, other cellulosic fibers such as cotton linters, trichomes, rayon, lyocell and bagasse fibers can be used in the fibrous structures of the present invention.

In addition to being useful as toilet tissue, facial tissue, paper towels and wipes, the DTAs may also be useful as hard surface, such as hardwood floor and/or linoleum, substrates, furniture wipes, glass wipes, all-purpose wipes, fitness equipment wipes, jewelry wipes, disinfecting wipes, automotive wipes, appliance wipes, toilet, tub and sink wipes and even preventive toxin, such as poison ivy/poison oak, wipes.

Personal Care Compositions and/or Devices

In one aspect, the compositions disclosed herein may be consumer products such as personal care compositions or devices. Such compositions can be applied to the skin and/or hair or in other embodiments used to treat and/clean a situs. The compositions can be, for example, formulated as bars, liquids, emulsions, shampoos, gels, powders, sticks, hair conditioners (rinse off and leave in), hair tonics, pastes, hair colorants, sprays, mousses, shaving products and other styling products.

The compositions of the present inventions may include the following components:

A. Detersive Surfactant

The composition of the present invention may include a detersive surfactant. The detersive surfactant component may comprise anionic detersive surfactant, zwitterionic or amphoteric detersive surfactant, or a combination thereof. The concentration of the anionic surfactant component in the composition should be sufficient to provide the desired cleaning and lather performance, and generally range from about 5% to about 50%.

Anionic surfactants suitable for use in the compositions are the alkyl and alkyl ether sulfates. Other suitable anionic detersive surfactants are the water-soluble salts of organic, sulfuric acid reaction products conforming to the formula [$R^1$—$SO_3$-M] where $R^1$ is a straight or branched chain, saturated, aliphatic hydrocarbon radical having from about 8 to about 24, or about 10 to about 18, carbon atoms; and M is a cation described hereinbefore. Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the compositions is the beta-alkyloxy alkane sulfonates. These surfactants conform to the Formula I:

Formula I

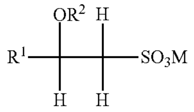

where $R^1$ is a straight chain alkyl group having from about 6 to about 20 carbon atoms, $R^2$ is a lower alkyl group having from about 1 to about 3 carbon atoms, or even 1 carbon atom, and M is a water-soluble cation as described hereinbefore.

U.S. Pat. Nos. 3,929,678, 2,658,072; 2,438,091; 2,528, 378.

B. Cationic Surfactant System

The composition of the present invention may comprise a cationic surfactant system. The cationic surfactant system can be one cationic surfactant or a mixture of two or more cationic surfactants. If present, the cationic surfactant system is included in the composition at a level by weight of from about 0.1% to about 10%, from about 0.5% to about 8%, from about 1% to about 5%, or even from about 1.4% to about 4%, in view of balance among ease-to-rinse feel, rheology and wet conditioning benefits.

A variety of cationic surfactants including mono- and di-alkyl chain cationic surfactants can be used in the compositions of the present invention. Examples of suitable materials include mono-alkyl chain cationic surfactants in view of the desired gel matrix and wet conditioning benefits. The mono-alkyl cationic surfactants are those having one long alkyl chain which has from 12 to 22 carbon atoms, from 16 to 22 carbon atoms, or a $C_{18}$-$C_{22}$ alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines. Mono-alkyl quaternary ammonium salts include, for example, those having a non-functionalized long alkyl chain. Mono-alkyl amines include, for example, mono-alkyl amidoamines and salts thereof.

Mono-long alkyl quaternized ammonium salts useful herein are those having the Formula (II):

Formula (II)

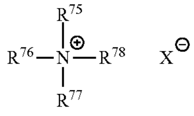

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. In one aspect, one of $R^{75}$, $R^{76}$, $R^{77}$ and $R^{78}$ is selected from an alkyl group of from 12 to 30 carbon atoms, in another aspect, from 16 to 22 carbon atoms, in another aspect, from 18 to 22 carbon atoms, or even 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Examples of suitable mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt. Among them, highly useful materials are behenyl trimethyl ammonium salt and stearyl trimethyl ammonium salt.

Mono-alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; in one aspect, l-glutamic acid, lactic acid, citric acid are highly useful. In one aspect, amines herein are partially neutralized with any of the acids at a molar ratio of the amine to the acid of from about 1:0.3 to about 1:2, or even from about 1:0.4 to about 1:1.

Although the mono-alkyl chain cationic surfactants are useful, other cationic surfactants such as di-alkyl chain cationic surfactants may also be used alone, or in combination with the mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

C. High Melting Point Fatty Compound

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section.

Among a variety of high melting point fatty compounds, fatty alcohols are used in one aspect the present invention. The fatty alcohols useful herein are those having from about 14 to about 30 carbon atoms, or even from about 16 to about 22 carbon atoms. These fatty alcohols are saturated and can be straight or branched chain alcohols. In one aspect, fatty alcohols include, for example, cetyl alcohol, stearyl alcohol, behenyl alcohol, and mixtures thereof.

High melting point fatty compounds of a single compound of high purity are typically used. In one aspect, single compounds of pure fatty alcohols selected from the group of pure cetyl alcohol, stearyl alcohol, and behenyl alcohol are employed. By "pure" herein, what is meant is that the compound has a purity of at least about 90%, or even at least about 95%. These single compounds of high purity provide good rinsability from the hair when the consumer rinses off the composition.

The high melting point fatty compound is included in the composition at a level of from about 0.1% to about 40%, from about 1% to about 30%, from about 1.5% to about 16% by weight of the composition, or even from about 1.5% to about 8% in view of providing improved conditioning benefits such as slippery feel during the application to wet hair, softness and moisturized feel on dry hair.

D. Cationic Polymers

The compositions of the present invention may contain a cationic polymer. Concentrations of the cationic polymer in the composition typically range from about 0.05% to about 3%, in another embodiment from about 0.075% to about 2.0%, and in yet another embodiment from about 0.1% to about 1.0%. Suitable cationic polymers will have cationic charge densities of at least about 0.5 meq/gm, in another embodiment at least about 0.9 meq/gm, in another embodiment at least about 1.2 meq/gm, in yet another embodiment at least about 1.5 meq/gm, but in one embodiment also less than about 7 meq/gm, and in another embodiment less than about 5 meq/gm, at the pH of intended use of the composition, which pH will generally range from about pH 3 to about pH 9, in one embodiment between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, in one embodiment between about 50,000 and about 5 million, and in another embodiment between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (in one aspect, secondary or tertiary), depending upon the particular species and the selected pH of the composition. Any anionic counter ion can be used in association with the cationic polymers so long as the polymers remain soluble in water, in the composition, or in a coacervate phase of the composition, and so long as the counter ions are physically and chemically compatible with the essential components of the composition or do not otherwise unduly impair product performance, stability or aesthetics. Non limiting examples of such counter ions include halides (e.g., chloride, fluoride, bromide, iodide), sulfate and methyl sulfate.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methyl acrylate (referred to in the industry by CTFA as Polyquaternium 47). In one aspect, cationic substituted monomers may be the cationic substituted dialkylaminoalkyl acrylamides, dialkylaminoalkyl methacrylamides, and combinations thereof. Such monomers conform the to the Formula III:

Formula III

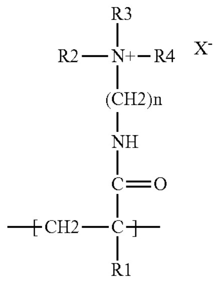

wherein $R^1$ is hydrogen, methyl or ethyl; each of $R^2$, $R^3$ and $R^4$ are independently hydrogen or a short chain alkyl having from about 1 to about 8 carbon atoms, from about 1 to about 5 carbon atoms, or even from about 1 to about 2 carbon atoms; n is an integer having a value of from about 1 to about 8, or even from about 1 to about 4; and X is a counter ion. The nitrogen attached to $R^2$, $R^3$ and $R^4$ may be a protonated amine (primary, secondary or tertiary), but is in one aspect, a quaternary ammonium wherein each of $R^2$, $R^3$ and $R^4$ are alkyl groups a non limiting example of which is polymethacrylamidopropyl trimonium chloride, available under the trade name Polycare®133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the Formula IV:

Formula IV

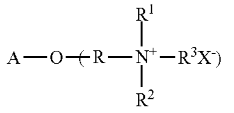

wherein A is an anhydroglucose residual group, such as a starch or cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) is typically about 20 or less; and X is an anionic counter ion as described in hereinbefore.

Useful cationic cellulose polymers include salts of hydroxyethyl cellulose reacted with trimethyl ammonium substituted epoxide, referred to in the industry (CTFA) as Polyquaternium 10 and available from Amerchol Corp. (Edison, N.J., USA) in their Ucare™ Polymer LR, Ucare™ Polymer JR, and Ucare™ Polymer KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the trade name Ucare™ Polymer LM-200.

Other suitable cationic polymers include cationic guar gum derivatives, such as guar hydroxypropyltrimonium chloride, specific examples of which include the Jaguar® series commercially available from Rhone-Poulenc Incorporated and the N-Hance® series commercially available from Aqualon Division of Hercules, Inc. Other suitable cationic polymers include quaternary nitrogen-containing cellulose ethers, some examples of which are described in U.S. Pat. No. 3,962,418. Other suitable polymers include synthetic polymers such as those disclosed in U.S. Publication No. 2007/0207109A1. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

E. Nonionic Polymers

The composition of the present invention may include a nonionic polymer. Polyalkylene glycols having a molecular weight of more than about 1000 are useful herein. Useful are those having the following general Formula V:

Formula V

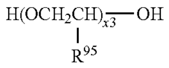

wherein $R^{95}$ is selected from the group consisting of H, methyl, and mixtures thereof. Polyethylene glycol polymers useful herein are PEG-2M (also known as Polyox WSR® N-10, which is available from Dow Chemical and as PEG-2,000); PEG-5M (also known as Polyox WSR® N-35 and Polyox WSR® N-80, available from Dow Chemical and as PEG-5,000 and Polyethylene Glycol 300,000); PEG-7M (also known as Polyox WSR® N-750 available from Dow Chemical); PEG-9M (also known as Polyox WSR® N-3333 available from Dow Chemical); and PEG-14 M (also known as Polyox WSR® N-3000 available from Dow Chemical).

F. Conditioning Agents

Conditioning agents, and in particular silicones, may be included in the composition. Conditioning agents include any material which is used to give a particular conditioning benefit to hair and/or skin. In hair treatment compositions, suitable conditioning agents are those which deliver one or more benefits relating to shine, softness, compatibility, antistatic properties, wet-handling, damage, manageability, body, and greasiness. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the compositions of the present invention can be an insoluble silicone conditioning agent. The silicone conditioning agent particles may comprise volatile silicone, non-volatile silicones, or combinations thereof. In one aspect, non-volatile silicones conditioning agents are employed. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, from about 0.1% to about 8%, from about 0.1% to about 5%, or even from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention typically have a viscosity, as measured at 25° C., from about 20 centistokes to about 2,000,000 centistokes ("cst"), from about 1,000 cst to about 1,800,000 cst, from about 50,000 cst to about 1,500,000 cst, or even from about 100,000 cst to about 1,500,000 csk.

The dispersed silicone conditioning agent particles typically have a number average particle diameter ranging from about 0.01 μm to about 50 μm. For small particle application to hair, the number average particle diameters typically range from about 0.01 μm to about 4 μm, from about 0.01 μm to about 2 μm, or even from about 0.01 μm to about 0.5 μm. For larger particle application to hair, the number average particle diameters typically range from about 4 μm to about 50 μm, from about 6 μm to about 30 μm, from about 9 μm to about 20 μm, or even from about 12 μm to about 18 μm.

a. Silicone Oils

Silicone fluids may include silicone oils, which are flowable silicone materials having a viscosity, as measured at 25° C., less than 1,000,000 cst, from about 5 cst to about 1,000,000 cst, or even from about 100 cst to about 600,000 cst. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

b. Amino and Cationic Silicones

Compositions of the present invention may include an aminosilicone. Aminosilicones, as provided herein, are silicones containing at least one primary amine, secondary amine, tertiary amine, or a quaternary ammonium group. Useful aminosilicones may have less than about 0.5% nitrogen by weight of the aminosilicone, less than about 0.2%, or even less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

In one aspect, the aminosilicones used in the present invention have a particle size of less than about 50μ once incorporated into the final composition. The particle size measurement is taken from dispersed droplets in the final composition. Particle size may be measured by means of a laser light scattering technique, using a Horiba model LA-930 Laser Scattering Particle Size Distribution Analyzer (Horiba Instruments, Inc.).

In one embodiment, the aminosilicone typically has a viscosity of from about 1,000 cst (centistokes) to about 1,000,000 cst, from about 10,000 to about 700,000 cst, from about 50,000 cst to about 500,000 cst, or even from about 100,000 cst to about 400,000 cst. This embodiment may also comprise a low viscosity fluid, such as, for example, those materials described below in Section F.(1). The viscosity of aminosilicones discussed herein is measured at 25° C.

In another embodiment, the aminosilicone typically has a viscosity of from about 1,000 cst to about 100,000 cst, from about 2,000 cst to about 50,000 cst, from about 4,000 cst to about 40,000 cst, or even from about 6,000 cst to about 30,000 cs.

The aminosilicone typically is contained in the composition of the present invention at a level by weight of from about 0.05% to about 20%, from about 0.1% to about 10%, and or even from about 0.3% to about 5%.

c. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

d. High Refractive Index Silicones

Other non-volatile, insoluble silicone fluid conditioning agents that are suitable for use in the compositions of the present invention are those known as "high refractive index silicones," having a refractive index of at least about 1.46, at least about 1.48, m at least about 1.52, or even at least about 1.55. The refractive index of the polysiloxane fluid will generally be less than about 1.70, typically less than about 1.60. In this context, polysiloxane "fluid" includes oils as well as gums and cyclic silicones such as those represented by Formula (VI) below:

Formula VI

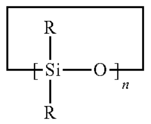

wherein R is as defined previously, and n is a number from about 3 to about 7, or even from about 3 to about 5.

Silicone fluids suitable for use in the compositions of the present invention are disclosed in U.S. Pat. No. 2,826,551, U.S. Pat. No. 3,964,500, and U.S. Pat. No. 4,364,837.

e. Silicone Resins

Silicone resins may be included in the conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

In one aspect, silicone resins for use in the compositions of the present invention include, but are not limited to MQ, MT, MTQ, MDT and MDTQ resins. In one aspect, Methyl is a highly suitable silicone substituent. In another aspect, silicone resins are typically MQ resins, wherein the M:Q ratio is typically from about 0.5:1.0 to about 1.5:1.0 and the average molecular weight of the silicone resin is typically from about 1000 to about 10,000.

f. Modified Silicones or Silicone Copolymers

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes; silicone aminopolyalkyleneoxide block copolymers disclosed in U.S. Pat. Nos. 5,807,956 and 5,981,681; hydrophilic silicone emulsions disclosed in U.S. Pat. No. 6,207,782; and polymers made up of one or more crosslinked rake or comb silicone copolymer segments disclosed in U.S. Pat. No. 7,465,439. Additional modified silicones or silicone copolymers useful herein are described in US Patent Application Nos. 2007/0286837A1 and 2005/0048549A1.

In alternative embodiments of the present invention, the above-noted silicone-based quaternary ammonium compounds may be combined with the silicone polymers described in U.S. Pat. Nos. 7,041,767 and 7,217,777 and US Application number 2007/0041929A1.

2. Organic Conditioning Oils

The compositions of the present invention may also comprise from about 0.05% to about 3%, from about 0.08% to about 1.5%, or even from about 0.1% to about 1%, of at least one organic conditioning oil as the conditioning agent, either alone or in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from about $C_{12}$ to about $C_{19}$. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of $C_4$ to about $C_{14}$ or even $C_6$ to about $C_{12}$. Suitable fatty esters include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

3. Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217,914, 4,381,919, and 4,422,853.

G. Anti-Dandruff Actives

The compositions of the present invention may also contain an anti-dandruff agent. Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff actives typically are pyridinethione salts. Such anti-dandruff particulate should be physically and chemically compatible with the essential components of the composition, and should not otherwise unduly impair product stability, aesthetics or performance.

Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

H. Humectant

The compositions of the present invention may contain a humectant. The humectants herein are selected from the group consisting of polyhydric alcohols, water soluble alkoxylated nonionic polymers, and mixtures thereof. The humectants, when used herein, are typically used at levels of from about 0.1% to about 20%, or even from about 0.5% to about 5%.

I. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, or even from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cyclonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with trade names Carbopol® 934, Carbopol® 940, Carbopol® 950, Carbopol® 980, and Carbopol® 981, all available from B.F. Goodrich Company, acrylates/steareth-20 methacrylate copolymer with trade name ACRYSOL™ 22 available from Rohm and Hass, nonoxynyl hydroxyethylcellulose with trade name Amercell™ POLYMER HM-1500 available from Amerchol, methylcellulose with trade name BENECEL®, hydroxyethyl cellulose with trade name NATROSOL®, hydroxypropyl cellulose with trade name KLUCEL®, cetyl hydroxyethyl cellulose with trade name POLYSURF® 67, all supplied by Hercules, ethylene oxide and/or propylene oxide based polymers with trade names CARBOWAX® PEGs, POLYOX® WASRs, and UCON® FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855.

These suspending agents include ethylene glycol esters of fatty acids in one aspect having from about 16 to about 22 carbon atoms. In one aspect, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

J. Aqueous Carrier

The formulations of the present invention can be in the form of pourable liquids (under ambient conditions). Such compositions will therefore typically comprise an aqueous carrier, which is present at a level of from about 20% to about 95%, or even from about 60% to about 85%. The aqueous carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

K. Dispersed Particles

The compositions may optionally comprise particles. The particles may be dispersed water-insoluble particles. The particles may be inorganic, synthetic, or semi-synthetic. In one embodiment, the particles have an average mean particle size of less than about 300 μm.

L. Gel Matrix

The above cationic surfactants, together with high melting point fatty compounds and an aqueous carrier, may form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, from about 1:1 to about 1:10, or even from about 1:1 to about 1:6.

M. Skin Care Actives

The composition may comprise at least one skin care active, useful for regulating and/or improving the condition and/or appearance of mammalian skin. The skin care active may be soluble in oil or water, and may be present primarily in the oil phase and/or in the aqueous phase. Suitable actives include, but are not limited to, vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals.

The composition may comprise from about 0.001% to about 10%, alternatively from about 0.01% to about 5%, of at least one vitamin. Herein, "vitamins" means vitamins, provitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, $C_1$-$C_{18}$ nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition may comprise a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

The composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EEMQRR; Argireline®), and Cu-histidine-glycine-glycine (Cu—HGG, also known as IAMIN®). The compositions may comprise from about $1\times10^{-7}$% to about 20%, alternatively from about $1\times10^{-6}$% to about 10%, and alternatively from about $1\times10^{-5}$% to about 5% of the peptide.

The composition may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). Other sugar amine compounds useful in skin care compositions include those described in U.S. Pat. No. 6,159,485, issued to Yu, et al. In one embodiment, the composition may comprise from about 0.01% to about 15%, alternatively from about 0.1% to about 10%, and alternatively from about 0.5% to about 5%, of the sugar amine.

The composition may comprise one or more sunscreen actives (or sunscreen agents) and/or ultraviolet light absorbers. Herein, suitable sunscreen actives include oil-soluble sunscreens, insoluble sunscreens, and water-soluble sunscreens. In certain embodiments, the composition may comprise from about 1% to about 20%, or, alternatively, from about 2% to about 10%, by weight of the composition, of the sunscreen active and/or ultraviolet light absorber. Exact amounts will vary depending upon the chosen sunscreen active and/or ultraviolet light absorber and the desired Sun Protection Factor (SPF), and are within the knowledge and judgment of one of skill in the art.

Non-limiting examples of suitable oil-soluble sunscreens include benzophenone-3, bis-ethylhexyloxyphenol methoxyphenyl triazine, butyl methoxydibenzoyl-methane, diethylamino hydroxy-benzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof.

Non-limiting examples of suitable insoluble sunscreens include methylene bis-benzotriazolyl tetramethylbutyl-phenol, titanium dioxide, zinc cerium oxide, zinc oxide, and derivatives and mixtures thereof.

Non-limiting examples of suitable water-soluble sunscreens include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyl-trimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquaternium-59, TEA-salicylate, and salts, derivatives and mixtures thereof.

The composition may comprise one or more compounds for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof. The compositions may comprise from about 0.0001% to about 15%, alternatively from about 0.01% to about 10%, alternatively from about 0.1% to about 5%, and alternatively from about 0.2% to about 2%, of an oil control agent.

The composition may comprise a tanning active. The compositions may comprise from about 0.1% to about 20%, from about 2% to about 7%, or, alternatively, from about 3% to about 6%, by weight of the composition, of a tanning active. A suitable tanning active includes dihydroxyacetone, which is also known as DHA or 1,3-dihydroxy-2-propanone.

The composition may comprise a safe and effective amount of one or more anti-acne actives. Examples of useful anti-acne actives include resorcinol, sulfur, salicylic acid, erythromycin, zinc, and benzoyl peroxide. Suitable anti-acne actives are described in further detail in U.S. Pat. No. 5,607,980. The composition may comprise a safe and effective amount of a desquamation active such as from about 0.01% to about 10%, from about 0.5% to about 5%, or, alternatively, from about 0.1% to about 2%, by weight of the composition. For example, the desquamation actives tend to improve the texture of the skin (e.g., smoothness). A suitable desquamation system may comprise sulfhydryl compounds and zwitterionic surfactants and is described in U.S. Pat. No. 5,681,852. Another suitable desquamation system may comprise salicylic acid and zwitterionic surfactants and is described in U.S. Pat. No. 5,652,228.

The composition may comprise a safe and effective amount of an anti-cellulite agent. Suitable agents may include, but are not limited to, xanthine compounds (e.g., caffeine, theophylline, theobromine, and aminophylline).

Skin care compositions may comprise a safe and effective amount of a chelating agent such as from about 0.1% to about 10% or from about 1% to about 5% of the composition. Exemplary chelators are disclosed in U.S. Pat. No. 5,487,884. A suitable chelator is furildioxime and derivatives.

The composition may comprise a skin lightening agent. The compositions may comprise from about 0.1% to about 10%, from about 0.2% to about 5%, or, alternatively, from about 0.5% to about 2%, by weight of the composition, of a skin lightening agent. Suitable skin lightening agents include kojic acid, arbutin, tranexamic acid, ascorbic acid and derivatives (e.g., magnesium ascorbyl phosphate or sodium ascorbyl phosphate or other salts of ascorbyl phosphate), ascorbyl glucoside, and the like. Other suitable skin lightening materials include undecylenoyl phenylalanine (Sepiwhite® from SEPPIC), aloesin, Actiwhite® (Cognis), and Emblica® (Rona).

The composition compositions may comprise a flavonoid. The flavonoid can be synthetic materials or obtained as extracts from natural sources, which also further may be derivatized. Examples of classes of suitable flavonoids are disclosed in U.S. Pat. No. 6,235,773.

The composition may comprise protease inhibitors including, but are not limited to, hexamidine compounds, vanillin acetate, menthyl anthranilate, soybean trypsin inhibitor, Bowman-Birk inhibitor, and mixtures thereof. Skin care compositions can include hexamidine compounds, its salts, and derivatives. As used herein, "hexaminide compound" means a compound having the Formula (VII):

Formula (VII)

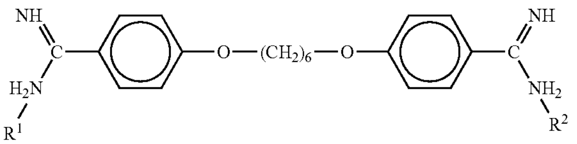

wherein $R^1$ and $R^2$ are optional or are organic acids (e.g., sulfonic acids, etc.). A particularly suitable hexamidine compound is hexamidine diisethionate.

The composition may other optional components such as non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobial or antifungal actives, and other useful skin care actives, which are described in further detail in U.S. application publication No. US 2006/0275237A1 and US 2004/0175347A1.

N. Color Cosmetics

The silicones of the present invention may also be used in cosmetic compositions, i.e., in products suitable for use in, on, or around the eyes, eyebrows, face, neck, chest, lips, hands, feet, or nails. Exemplary cosmetic products include eye liners, eye shadows, eyebrow pencils, mascaras, eye makeup removers, false eyelashes, under-eye concealers, eye creams, concealers, correctors, primers, blushes, bronzers, highlighters, shimmers, foundations, powders, sunscreens, brushes, face creams, lip primers, lip pencils, lipsticks, lip glosses, lip balms, lip stains, lip creams, and lotions. Examples of cosmetic products are found in U.S. Pat. No. 6,325,995 directed to an exemplary lip product; and U.S. Pat. No. 6,696,049 directed to an exemplary face product; and U.S. Pat. No. 6,503,495. The silicones of the present invention may be combined with materials commonly found in these compositions, such as alkyl dimethicone copolyols, polyols, hydrophilic skin treatment agents, carriers, thickening agent (such as solid waxes, gelling agents, inorganic thickeners, oil soluble polymers, fatty compounds, and mixtures thereof), pigments, film forming agents, preservatives, vitamins, etc. See U.S. Pat. No. 7,270,828 for examples.

O. Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their salts and/or derivatives, water insoluble amino acids such as tyrosine, tryptamine, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, vitamins, niacinamide, caffeine and minoxidil.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions of the present invention may also contain antimicrobial agents which are useful as cosmetic biocides.

The compositions of the present invention may also contain chelating agents.

Method of Making Shampoo Formulations

Any suitable method of making the shampoo of the present invention may be used. In one embodiment, undecyl-based surfactant is blended with the other components of the shampoo compositions, according to standard methods known in the art. The typical procedure used for a clarifying shampoo would be to combine the undecyl sulfate paste or undeceth sulfate paste or mixtures thereof with water, add the desired water soluble co-surfactant and finish the composition by the addition preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the surfactant mixture prior the finishing step.

In the case of conditioning shampoos, typically the surfactant paste is combined with the co-surfactant as above and diluted with water to a target level commensurate to achieving the final activity. Rheology modifiers can be added at this point followed by conditioning agents, e.g. sucrose polyesters, silicones or silicone emulsions or other oils, cationic polymers from polymer premixes, perfumes, pearlizing agents or opacifiers, perfumes, and preservatives. Appropriate mixing steps to insure homogeneity are used as needed. The product is finished by the addition of pH control agents, hydrotropes, and salts to the desired physical properties.

Method of Making Conditioner Formulations

The hair conditioners can be prepared by any conventional method well known in the art. They are suitably made as follows: deionized water is heated to 85° C. and cationic surfactants and high melting point fatty compounds are mixed in. If necessary, cationic surfactants and fatty alcohols can be pre-melted at 85° C. before addition to the water. The water is maintained at a temperature of about 85° C. until the components are homogenized, and no solids are observed. The mixture is then cooled to about 55° C. and maintained at this temperature, to form a gel matrix. Silicones, or a blend of silicones and a low viscosity fluid, or an aqueous dispersion of a silicone is added to the gel matrix. When included, poly alpha-olefin oils, polypropylene glycols, and/or polysorbates are also added to the gel matrix. When included, other additional components such as perfumes and preservatives are added with agitation. The gel matrix is maintained at about 50° C. during this time with constant stifling to assure homogenization. After it is homogenized, it is cooled to room temperature. A triblender and/or mill can be used in each step, if necessary to disperse the materials.

Compact Formulations

The present invention can also be used in a compact hair care formulation. A compact formula is a formula which delivers the same benefit to the consumer at a lower usage level. Compact formulations and methods of making compact formulations are described in US Application Publication No 2009/0221463A1.

Shampoo Examples

| | EXAMPLE COMPOSITION | | |
|---|---|---|---|
| Ingredient | I | II | III |
| Water | q.s. | q.s. | q.s. |
| Polyquaternium 76[1] | 2.50 | — | — |

-continued

| | EXAMPLE COMPOSITION | | |
|---|---|---|---|
| Ingredient | I | II | III |
| Guar, Hydroxypropyl Trimonium Chloride[2] | — | 0.25 | — |
| Polyquaternium 6[3] | — | — | 0.79 |
| Sodium Laureth Sulfate (SLE3S)[4] | 21.43 | 21.43 | 21.43 |
| Sodium Lauryl Sulfate (SLS)[5] | 20.69 | 20.69 | 20.69 |
| Alkene Siloxane Polymer[6] | 0.75 | 1.00 | 0.5 |
| Cocoamidopropyl Betaine[7] | 3.33 | 3.33 | 3.33 |
| Cocoamide MEA[8] | 1.0 | 1.0 | 1.0 |
| Ethylene Glycol Distearate[9] | 1.50 | 1.50 | 1.50 |
| Sodium Chloride[10] | 0.25 | 0.25 | 0.25 |
| Fragrance | 0.70 | 0.70 | 0.70 |
| Preservatives, pH adjusters | Up to 1% | Up to 1% | Up to 1% |

[1]Mirapol ® AT-1, Copolymer of Acrylamide(AM) and TRIQUAT, MW = 1,000,000; CD = 1.6 meq./gram; 10% active; Supplier Rhodia
[2]Jaguar ® C500, MW - 500,000, CD = 0.7, supplier Rhodia
[3]Mirapol ® 100S, 31.5% active, supplier Rhodia
[4]Sodium Laureth Sulfate, 28% active, supplier: P&G
[5]Sodium Lauryl Sulfate, 29% active supplier: P&G
[6]Alkene Siloxane Polymer of Example 1-15 (mixtures thereof may also be used)
[7]Tegobetaine F-B, 30% active supplier: Goldschmidt Chemicals
[8]Monamid ® CMA, 85% active, supplier Goldschmidt Chemical
[9]Ethylene Glycol Distearate, EGDS Pure, supplier Goldschmidt Chemical
[10]Sodium Chloride USP (food grade), supplier Morton; note that salt is an adjustable ingredient, higher or lower levels may be added to achieve target viscosity.

| | EXAMPLE COMPOSITION | | |
|---|---|---|---|
| Ingredient | I | II | III |
| Water | q.s. | q.s. | q.s. |
| Alkene Siloxane Polymer[1] | 1.0 | — | — |
| Alkene Siloxane Polymer[1] | — | 0.5 | — |
| Alkene Siloxane Polymer[1] | — | — | 0.5 |
| Cyclopentasiloxane[2] | — | 0.61 | 1.5 |
| Behenyl trimethyl ammonium chloride[3] | 2.25 | 2.25 | 2.25 |
| Isopropyl alcohol | 0.60 | 0.60 | 0.60 |
| Cetyl alcohol[4] | 1.86 | 1.86 | 1.86 |
| Stearyl alcohol[5] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/ Methylisothiazolinone[6] | 0.0005 | 0.0005 | 0.0005 |
| Panthenol[7] | 0.10 | 0.10 | 0.10 |
| Panthenyl ethyl ether[8] | 0.05 | 0.05 | 0.05 |
| Fragrance | 0.35 | 0.35 | 0.35 |

[1]Alkene Siloxane Polymer of Example 1-15 (mixtures thereof may also be used)
[2]Cyclopentasiloxane: SF1202 available from Momentive Performance Chemicals
[3]Behenyl trimethyl ammonium chloride/Isopropyl alcohol: Genamin ™ KMP available from Clariant
[4]Cetyl alcohol: Konol ™ series available from Shin Nihon Rika
[5]Stearyl alcohol: Konol ™ series available from Shin Nihon Rika
[6]Methylchloroisothiazolinone/Methylisothiazolinone: Kathon ™ CG available from Rohm & Haas
[7]Panthenol: Available from Roche
[8]Panthenyl ethyl ether: Available from Roche Body Cleansing Compositions

| | A | B | C |
|---|---|---|---|
| sodium laureth sulfate 3 mol ethoxylated (29%, P & G Chemicals, Cincinnati, OH) | 6.8 | 6.8 | 6.8 |
| sodium lauryl sulfate (28%, P & G) | 2.6 | 2.6 | 2.6 |

-continued

| | | | |
|---|---|---|---|
| cocamidopropyl betaine (MIRATAINE ® CAB/AS, Rhodia Inc.) | 1.0 | 1.0 | 1.0 |
| citric acid anhydrous | 0.16 | 0.16 | 0.16 |
| disodium EDTA (DISSOLVINE ™ NA 2x from Akzo Nobel) | 0.1 | 0.1 | 0.1 |
| sodium benzoate (PUROX ™ S Grains from DSM N.V. Corp.) | 0.26 | 0.26 | 0.26 |
| methylchloroisothiazolinone and methylisothiazolinone (KATHON ™ CG from Rohm & Haas) | 0.0005 | 0.0005 | 0.0005 |
| sodium chloride | 3.4 | 3.4 | 3.4 |
| Alkene Siloxane polymer of Example 1-15 (mixtures thereof may also be used) | 2.0 | 5.0 | 10.0 |
| polyquaternium 76, COUG 5 AM:TRIQUAT(95:5) (10% aq., Rhodia Inc., Hillsborough, NJ, USA) | 0.3 | 0.3 | 0.3 |
| water | Q.S. | Q.S. | Q.S. |

| | Example D | Example E | Example F |
|---|---|---|---|
| I: Cleansing Phase Composition | | | |
| Sodium Trideceth Sulfate (sulfated from Iconol ® TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance ® 3196 from Aqualon) | — | 0.3 | 0.7 |
| Guar Hydroxypropyltrimonium Chloride (Jaguar ® C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconol ® TDA-3 from BASF Corp.) | 1.75 | 1.75 | 1.75 |
| Methyl chloro isothiazolinone and methyl isothiazolinone (Kathon ™ CG, Rohm & Haas) | 0.033 | 0.033 | 0.033 |
| EDTA (Dissolvine ™ NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite ® 1000 from Sonnerbonn) | 20 | 20 | 20 |
| Alkene Siloxane Polymer of Example 1-15 (mixtures thereof may also be used) | 10 | 10 | 10 |
| III: Surfactant Phase:Benefit Phase Blending Ratio | 50:50 | 90:10 | 90:10 |

Skin Care

Examples 1-2

The following are non-limiting examples of compositions that may be applied to keratinous tissue in accordance with the methods described herein.

| | Example | |
|---|---|---|
| | 1 | 2 |
| PHASE A | | |
| DC-9040[1] Dimethicone | 13.5 | 3.00 |
| Polymethylsilsesquioxane[2] | 7.5 | 4.00 |
| Cyclomethicone | 19 | 3.00 |
| KSG-210[3] | 2.5 | 2.75 |

-continued

| | Example | |
|---|---|---|
| | 1 | 2 |
| Alkene Siloxane Polymer of Example 1-15 (mixtures thereof may also be used) | 4 | 4 |
| Abil EM97[4] | 0.50 | |
| KF 6017[5] | 0.40 | |
| Cetyl Ricinoleate | 0.25 | |
| Fragrance | 0.10 | 0.10 |
| PHASE B | | |
| Glycerin | 7.00 | 10.00 |
| Panthenol | 1.00 | 0.5 |
| Pentylene Glycol | | 3.00 |
| Propylene Glycol | 1.00 | |
| Butylene Glycol | 1.00 | |

-continued

| | Example | |
|---|---|---|
| | 1 | 2 |
| Tocopherol Acetate | 0.50 | |
| Citric Acid | | |
| Sodium Citrate | | |
| Sodium Benzoate | | |
| Niacinamide | 1.00 | 5.00 |
| Methylparaben | 0.20 | 0.25 |
| Benzyl Alcohol | 0.50 | |
| Propyl Paraben | 0.10 | |
| Disodium EDTA | 0.10 | |
| Sodium Chloride | | 0.50 |
| Titanium Dioxide Dispersion[6] | | 0.5 |
| Water | q.s to 100 | q.s to 100 |

[1]12.5% Dimethicone Crosspolymer in Cyclopentasiloxane. Available from Dow Corning
[2]E.g. Tospearl ® 145A or Tospearl ® 2000. Available from GE Toshiba Silicone
[3]25% Dimethicone PEG-10/15 Crosspolymer in Dimethicone. Available from Shin-Etsu
[4]Bis-PEG/PPG-14/14 Dimethicone. Available from Degussa
[5]PEG-10 Dimethicone. Available from Shin-Etsu
[6]75% Titanium Dioxide and Water and Glycerin and Ammonium Polyacrylate from Kobo Products, Inc.

Deodorant Examples

The following examples further describe and demonstrate embodiments within the scope of the present invention. The examples are given solely for the purpose of illustration and are not to be construed as limitations of the present invention as many variations thereof are possible without departing from the spirit and scope of the invention.

| Ingredient | Example 1 | Example 2 | Example 3 |
|---|---|---|---|
| Part I: Partial Continuous Phase | | | |
| Cyclopentasiloxane[1] | 17.65 | | 16.65 |
| DC5200[2] | 1.20 | 1.20 | 1.20 |
| Fragrance | 1.35 | 1.75 | 1.35 |
| Hexyl Methicone[3] | | 17.25 | |
| Mineral oil | | | |
| Alkene Siloxane Polymer of Example 1-15 (mixtures thereof may also be used) | 5 | 5 | 5 |
| Part II: Disperse Phase | | | |
| ACH (50% solution) | 40.00 | 40.00 | 40.00 |
| ZAG (30% solution) | | | |
| propylene glycol | 5.00 | 5.00 | 5.00 |
| water | 12.30 | 12.30 | 12.30 |
| Part III: Structurant Plus Remainder of Continuous Phase | | | |
| FinSolve ® TN | 6.50 | 6.50 | 6.50 |
| Ozocrite Wax | | | 12 |
| Performalene ® PL[4] | 11.00 | 11.00 | |

[1]DC 246 fluid from Dow Corning
[2]from Dow Corning
[3]41M10 from Cognis
[4]from New Phase Technologies All of these examples can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with suitable mill, for example a Greeco 1L03 from Greeco Corp, to create a homogenous emulsion. Part III is mixed and heated to 88° C. until the all solids are completely melted. The emulsion is then also heated to 88° C., and Part 3 ingredients are slowly added to the emulsion. The final mixture is then poured into an appropriate container, and allowed to solidify and cool to ambient temperature.

Fabric and/or Hard Surface Cleaning and/or Treatment Compositions

Aspects of the invention include the use of the organosilicone polymers disclosed herein in laundry detergent compositions (e.g., TIDE™), hard surface cleaners (e.g., MR CLEAN™) automatic dishwashing liquids (e.g., CASCADE™), dishwashing liquids (e.g., DAWN™), and floor cleaners (e.g., SWIFFER™). Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445. The cleaning compositions disclosed herein are typically formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

Fabric treatment compositions disclosed herein typically comprise a fabric softening active ("FSA") and an organosilicone polymer disclosed herein. Suitable fabric softening actives, include, but are not limited to, materials selected from the group consisting of quats, amines, fatty esters, sucrose esters, silicones, dispersible polyolefins, clays, polysaccharides, fatty oils, polymer latexes and mixtures thereof.

Adjunct Materials

The disclosed compositions may include additional adjunct ingredients. Each adjunct ingredient is not essential to Applicants' compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below. The following is a non-limiting list of suitable additional adjuncts.

Deposition Aid—In one aspect, the fabric treatment composition may comprise from about 0.01% to about 10%, from about 0.05 to about 5%, or from about 0.15 to about 3% of a deposition aid. Suitable deposition aids are disclosed in, for example, U.S. patent Ser. No. 12/080,358.

In one aspect, the deposition aid may be a cationic or amphoteric polymer. In another aspect, the deposition aid may be a cationic polymer. Cationic polymers in general and their method of manufacture are known in the literature. In one aspect, the cationic polymer may have a cationic charge density of from about 0.005 to about 23 meq/g, from about 0.01 to about 12 meq/g, or from about 0.1 to about 7 meq/g, at the pH of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers.

Non-limiting examples of deposition enhancing agents are cationic or amphoteric, polysaccharides, proteins and synthetic polymers. Cationic polysaccharides include cationic cellulose derivatives, cationic guar gum derivatives, chitosan and derivatives and cationic starches. Cationic polysaccharides have a molecular weight from about 50,000 to about 2 million, or even from about 100,000 to about 3,500,000. Suitable cationic polysaccharides include cationic cellulose ethers, particularly cationic hydroxyethylcellulose and cationic hydroxypropylcellulose. Examples of cationic hydroxyalkyl cellulose include those with the INCI name Polyquaternium10 such as those sold under the trade names Ucare™ Polymer JR 30M, JR 400, JR 125, LR 400 and LK 400 polymers; Polyquaternium 67 such as those sold under the trade name Softcat SK™, all of which are marketed by Amerchol Corporation, Edgewater N.J.; and Polyquaternium 4 such as those sold under the trade name Celquat™ H200 and Celquat™ L-200 available from National Starch and Chemical Company, Bridgewater, N.J. Other suitable polysaccharides include Hydroxyethyl cellulose or hydroxypropylcellulose quaternized with glycidyl $C_{12}$-$C_{22}$ alkyl dimethyl ammonium chloride. Examples of such polysaccharides include the polymers with the INCI names Polyquaternium 24 such as those sold under the trade name Quaternium LM 200 by Amerchol Corporation, Edgewater N.J. Cationic starches described by D. B. Solarek in Modified Starches, Properties and Uses published by CRC Press (1986) and in U.S. Pat. No. 7,135,451, col. 2, line 33-col. 4, line 67. Cationic galactomannans include cationic guar gums or cationic locust bean gum. An example of a cationic guar gum is a quaternary ammonium derivative of Hydroxypropyl Guar such as those sold under the trade name Jaguar®C13 and Jaguar®Excel available from Rhodia, Inc of Cranbury N.J. and N-Hance® by Aqualon, Wilmington, Del.

Another group of suitable cationic polymers includes those produced by polymerization of ethylenically unsaturated monomers using a suitable initiator or catalyst, such as those disclosed in U.S. Pat. No. 6,642,200.

Suitable polymers may be selected from the group consisting of cationic or amphoteric polysaccharide, polyethylene imine and its derivatives, and a synthetic polymer made by polymerizing one or more cationic monomers selected from the group consisting of N,N-dialkylaminoalkyl acrylate, N,N-dialkylaminoalkyl methacrylate, N,N-dialkylaminoalkyl acrylamide, N,N-dialkylaminoalkylmethacrylamide, quaternized N,N dialkylaminoalkyl acrylate quaternized N,N-dialkylaminoalkyl methacrylate, quaternized N,N-dialkylaminoalkyl acrylamide, quaternized N,N-dialkylaminoalkylmethacrylamide, Methacryloamidopropyl-pentamethyl-1,3-propylene-2-ol-ammonium dichloride, N,N,N,N',N',N",N"-heptamethyl-N"-3-(1-oxo-2-methyl-2-propenyl) aminopropyl-9-oxo-8-azo-decane-1,4,10-triammonium trichloride, vinylamine and its derivatives, allylamine and its derivatives, vinyl imidazole, quaternized vinyl imidazole and diallyl dialkyl ammonium chloride and combinations thereof, and optionally a second monomer selected from the group consisting of acrylamide, N,N-dialkyl acrylamide, methacrylamide, N,N-di alkylmethacrylamide, C1-C12 alkyl acrylate, C1-C12 hydroxyalkyl acrylate, polyalkylene glyol acrylate, C1-C12 alkyl methacrylate, C1-C12 hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and derivatives, acrylic acid, methacrylic acid, maleic acid, vinyl sulfonic acid, styrene sulfonic acid, acrylamidopropylmethane sulfonic acid (AMPS) and their salts. The polymer may optionally be branched or cross-linked by using branching and crosslinking monomers. Branching and crosslinking monomers include ethylene glycoldiacrylate divinylbenzene, and butadiene. In another aspect, the treatment composition may comprise an amphoteric deposition aid polymer so long as the polymer possesses a net positive charge. Said polymer may have a cationic charge density of about 0.05 to about 18 milliequivalents/g.

In another aspect, the deposition aid may be selected from the group consisting of cationic polysaccharide, polyethylene imine and its derivatives, poly(acrylamide-co-diallyldimethylammonium chloride), poly(acrylamide-methacrylamidopropyltrimethyl ammonium chloride), poly(acrylamide-co-N,N-dimethyl aminoethyl acrylate) and its quaternized derivatives, poly(acrylamide-co-N,N-dimethyl aminoethyl methacrylate) and its quaternized derivative, poly(hydroxyethylacrylate-co-dimethyl aminoethyl methacrylate), poly(hydroxpropylacrylate-co-dimethyl aminoethyl methacrylate), poly(hydroxpropylacrylate-co-methacrylamidopropyltrimethylammonium chloride), poly(acrylamide-co-diallyldimethylammonium chloride-co-acrylic acid), poly(acrylamide-methacrylamidopropyltrimethyl ammonium chloride-co-acrylic acid), poly(diallyldimethyl ammonium chloride), poly(vinylpyrrolidone-co-dimethylaminoethyl methacrylate), poly(ethyl methacrylate-co-quaternized dimethylaminoethyl methacrylate), poly(ethyl methacrylate-co-oleyl methacrylate-co-diethylaminoethyl methacrylate), poly(diallyldimethylammonium chloride-co-acrylic acid), poly(vinyl pyrrolidone-co-quaternized vinyl imidazole) and poly(acrylamide-co-Methacryloamidopropyl-pentamethyl-1,3-prop ylene-2-ol-ammonium dichloride), Suitable deposition aids include Polyquaternium-1, Polyquaternium-5, Polyquaternium-6, Polyquaternium-7, Polyquaternium-8, Polyquaternium-11, Polyquaternium-14, Polyquaternium-22, Polyquaternium-28, Polyquaternium-30, Polyquaternium-32 and Polyquaternium-33, as named under the International Nomenclature for Cosmetic Ingredients. In one aspect, the deposition aid may comprise polyethyleneimine or a polyethyleneimine derivative. A suitable polyethyleneinine useful herein is that sold under the trade name Lupasol® by BASF, AG, and Ludwigshafen, Germany In another aspect, the deposition aid may comprise a cationic acrylic based polymer. In a further aspect, the deposition aid may comprise a cationic polyacrylamide. In another aspect, the deposition aid may comprise a polymer comprising polyacrylamide and polymethacrylamidopropyl trimethylammonium cation. In another aspect, the deposition aid may comprise poly(acrylamide-N-dimethyl aminoethyl acrylate) and its quaternized derivatives. In this aspect, the deposition aid may be that sold under the trade name Sedipur®, available from BTC Specialty Chemicals, a BASF Group, Florham Park, N.J. In a yet further aspect, the deposition aid may comprise poly(acrylamide-co-methacrylamidopropyltrimethyl ammonium chloride). In another aspect, the deposition aid may comprise a non-acrylamide based polymer, such as that sold under the trade name Rheovis® CDE, available from Ciba Specialty Chemicals, a BASF group, Florham Park, N.J., or as disclosed in USPA 2006/0252668.

In another aspect, the deposition aid may be selected from the group consisting of cationic or amphoteric polysaccharides. In one aspect, the deposition aid may be selected from the group consisting of cationic and amphoteric cellulose ethers, cationic or amphoteric galactomannan, cationic guar gum, cationic or amphoteric starch, and combinations thereof Another group of suitable cationic polymers may include alkylamine-epichlorohydrin polymers which are reaction products of amines and oligoamines with epichlorohydrin, for example, those polymers listed in, for example, U.S. Pat. Nos. 6,642,200 and 6,551,986. Examples include dimethylamine-epichlorohydrin-ethylenediamine, available under the trade name Cartafix® CB and Cartafix® TSF from Clariant, Basle, Switzerland.

Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin. They are available from Hercules Inc. of Wilmington Del. under the trade name Kymene™ or from BASF AG (Ludwigshafen, Germany) under the trade name Luresin™. The cationic polymers may contain charge neutralizing anions such that the overall polymer is neutral under ambient conditions. Non-limiting examples of suitable counter ions (in addition to anionic species generated during use) include chloride, bromide, sulfate, methylsulfate, sulfonate, methylsulfonate, carbonate, bicarbonate, formate, acetate, citrate, nitrate, and mixtures thereof.

The weight-average molecular weight of the polymer may be from about 500 Daltons to about 5,000,000 Daltons, or from about 1,000 Daltons to about 2,000,000 Daltons, or from about 2,500 Daltons to about 1,500,000 Daltons, as determined by size exclusion chromatography relative to polyethylene oxide standards with RI detection. In one aspect, the MW of the cationic polymer may be from about 500 Daltons to about 37,500 Daltons.

Surfactants: The products of the present invention may comprise from about 0.11% to 80% by weight of a surfactant. In one aspect, such compositions may comprise from about 5% to 50% by weight of surfactant. Surfactants utilized can be of the anionic, nonionic, zwitterionic, ampholytic or cationic type or can comprise compatible mixtures of these types. Detergent surfactants useful herein are described in U.S. Pat. Nos. 3,664,961, 3,919,678, 4,222,905, 4,239,659, 6,136,769, 6,020,303, and 6,060,443.

Anionic and nonionic surfactants are typically employed if the fabric care product is a laundry detergent. On the other hand, cationic surfactants are typically employed if the fabric care product is a fabric softener.

Useful anionic surfactants can themselves be of several different types. For example, water-soluble salts of the higher fatty acids, i.e., "soaps", are useful anionic surfactants in the compositions herein. This includes alkali metal soaps such as the sodium, potassium, ammonium, and alkylolammonium salts of higher fatty acids containing from about 8 to about 24 carbon atoms, or even from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Useful anionic surfactants include the water-soluble salts, particularly the alkali metal, ammonium and alkylolammonium (e.g., monoethanolammonium or triethanolammonium) salts, of organic sulfuric reaction products having in their molecular structure an alkyl group containing from about 10 to about 20 carbon atoms and a sulfonic acid or sulfuric acid ester group. (Included in the term "alkyl" is the alkyl portion of aryl groups.) Examples of this group of synthetic surfactants are the alkyl sulfates and alkyl alkoxy sulfates, especially those obtained by sulfating the higher alcohols ($C_8$-$C_{18}$ carbon atoms).

Other useful anionic surfactants herein include the water-soluble salts of esters of $\alpha$-sulfonated fatty acids containing from about 6 to 20 carbon atoms in the fatty acid group and from about 1 to 10 carbon atoms in the ester group; water-soluble salts of 2-acyloxy-alkane-1-sulfonic acids containing from about 2 to 9 carbon atoms in the acyl group and from about 9 to about 23 carbon atoms in the alkane moiety; water-soluble salts of olefin sulfonates containing from about 12 to 24 carbon atoms; and 13-alkyloxy alkane sulfonates containing from about 1 to 3 carbon atoms in the alkyl group and from about 8 to 20 carbon atoms in the alkane moiety.

In another embodiment, the anionic surfactant may comprise a $C_{11}$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, having an average degree of alkoxylation of from 1 to 30, wherein the alkoxy comprises a $C_1$-$C_4$ chain and mixtures thereof; a mid-chain branched alkyl sulfate surfactant; a mid-chain branched alkyl alkoxy sulfate surfactant having an average degree of alkoxylation of from 1 to 30, wherein the alkoxy comprises a $C_1$-$C_4$ chain and mixtures thereof; a $C_{10}$-$C_{18}$ alkyl alkoxy carboxylates comprising an average degree of alkoxylation of from 1 to 5; a $C_{12}$-$C_{20}$ methyl ester sulfonate surfactant, a $C_{10}$-$C_{18}$ alpha-olefin sulfonate surfactant, a $C_6$-$C_{20}$ sulfosuccinate surfactant, and a mixture thereof.

In addition to the anionic surfactant, the fabric care compositions of the present invention may further contain a nonionic surfactant. The compositions of the present invention can contain up to about 30%, alternatively from about 0.01% to about 20%, more alternatively from about 0.1% to about 10%, by weight of the composition, of a nonionic surfactant. In one embodiment, the nonionic surfactant may comprise an ethoxylated nonionic surfactant. Examples of suitable nonionic surfactants are provided in U.S. Pat. Nos. 4,285,841, 6,150,322, and 6,153,577.

Suitable for use herein are the ethoxylated alcohols and ethoxylated alkyl phenols of the formula $R(OC_2H_4)n\ OH$, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)nOH$, wherein R1 is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

Additional suitable nonionic surfactants include polyhydroxy fatty acid amides such as N-methyl N-1-deoxyglucityl cocoamide and N-methyl N-1-deoxyglucityl oleamide and alkyl polysaccharides such as the ones described in U.S. Pat. No. 5,332,528. Alkylpolysaccharides are disclosed in U.S. Pat. No. 4,565,647.

The fabric care compositions of the present invention may contain up to about 30%, alternatively from about 0.01% to about 20%, more alternatively from about 0.1% to about 20%, by weight of the composition, of a cationic surfactant. For the purposes of the present invention, cationic surfactants include those which can deliver fabric care benefits. Non-limiting examples of useful cationic surfactants include: fatty amines; quaternary ammonium surfactants; and imidazoline quat materials.

In some embodiments, useful cationic surfactants, include those disclosed in U.S. Patent Application number 2005/0164905 A1 and having the general Formula (VIII):

Formula (VIII)

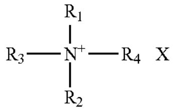

wherein:

(a) $R_1$ and $R_2$ each are individually selected from the groups of: $C_1$-$C_4$ alkyl; $C_1$-$C_4$ hydroxy alkyl; benzyl; $—(CnH_{2n}O)_xH$, wherein:

i. x has a value from about 2 to about 5;

ii. n has a value of about 1-4;

(b) $R_3$ and $R_4$ are each:

i. a $C_8$-$C_{22}$ alkyl; or ii. $R_3$ is a $C_8$-$C_{22}$ alkyl and $R_4$ is selected from the group of: $C_1$-$C_{10}$ alkyl; $C_1$-$C_{10}$ hydroxy alkyl; benzyl; $—(CnH_{2n}O)_xH$, wherein:

1. x has a value from 2 to 5; and
2. n has a value of 1-4; and (c) X is an anion.

Fabric Softening Active Compounds—The fabric softening active may comprise, as the principal active, compounds of the following Formula (IX)

$$\{R_{4-m}—N^+—[X—Y—R^1]_m\}X^-$$ Formula (IX)

wherein each R may comprise either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each X may independently be $(CH_2)_n$, $CH_2—CH(CH_3)—$ or $CH—(CH_3)—CH_2—$; each Y may comprise —O—(O)C—, —C(O)—O—, —NR—C(O)—, or —C(O)—NR—; each m may be 2 or 3; each n may be from 1 to about 4, in one aspect 2; the sum of carbons in each $R^1$, plus one when Y is —O—(O)C— or —NR—C(O)—, may be $C_{12}$-$C_{22}$, or $C_{14}$-$C_{20}$, with each $R^1$ being a hydrocarbyl, or substituted hydrocarbyl group; and $X^-$ may comprise any softener-compatible anion. In one aspect, the softener-compatible anion may comprise chloride, bromide, methylsulfate, ethylsulfate, sulfate, and nitrate. In another aspect, the softener-compatible anion may comprise chloride or methyl sulfate.

In another aspect, the fabric softening active may comprise the general Formula (X):

$$[R_3N^+CH_2CH(YR^1)(CH_2YR^1)]X^-$$ Formula (X)

wherein each Y, R, $R^1$, and $X^-$ have the same meanings as before. Such compounds include those having the Formula (XI):

$$[CH_3]_3N^{(+)}[CH_2CH(CH_2O(O)CR^1)O(O)CR^1]Cl^{(-)}$$ Formula (XI)

wherein each R may comprise a methyl or ethyl group. In one aspect, each $R^1$ may comprise a $C_{15}$ to $C_{19}$ group. As used herein, when the diester is specified, it can include the monoester that is present.

These types of agents and general methods of making them are disclosed in U.S. Pat. No. 4,137,180. An example of a suitable DEQA (2) is the "propyl" ester quaternary ammonium fabric softener active comprising the formula 1,2-di (acyloxy)-3-trimethylammoniopropane chloride.

In one aspect, the fabric softening active may comprise the Formula (XII):

$$[R_{4-m}—N^+—R^1{}_m]X^-$$ Formula (XII)

wherein each R, $R^1$, m and $X^-$ have the same meanings as before.

In a further aspect, the fabric softening active may comprise the Formula (XIII):

Formula (XIII)

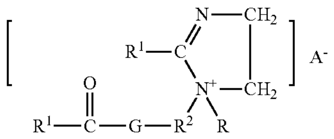

wherein each R and $R^1$ have the definitions given above; $R^2$ may comprise a $C_{1-6}$ alkylene group, in one aspect an ethylene group; and G may comprise an oxygen atom or an —NR— group; and $A^-$ is as defined below.

In a yet further aspect, the fabric softening active may comprise the Formula (XIV):

Formula (XIV)

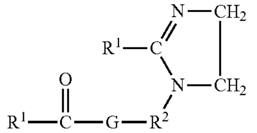

wherein $R^1$, $R^2$ and G are defined as above.

In a further aspect, the fabric softening active may comprise condensation reaction products of fatty acids with dialkylenetriamines in, e.g., a molecular ratio of about 2:1, said reaction products containing compounds of the Formula (XV):

$$R^1—C(O)—NH—R^2—NH—R^3—NH—C(O)—R^1$$ Formula (XV)

wherein $R^1$, $R^2$ are defined as above, and $R^3$ may comprise a $C_{1-6}$ alkylene group, or an ethylene group and wherein the reaction products may optionally be quaternized by the additional of an alkylating agent such as dimethyl sulfate. Such quaternized reaction products are described in additional detail in U.S. Pat. No. 5,296,622.

In a yet further aspect, the fabric softening active may comprise the Formula (XVI):

$$[R^1—C(O)—NR—R^2—N(R)_2—R^3—NR—C(O)—R^1]^+A^-$$ Formula (XVI)

wherein R, $R^1$, $R^2$, and $R^3$ are defined as above; $A^-$ is as defined below.

In a yet further aspect, the fabric softening active may comprise reaction products of fatty acid with hydroxyalkylalkylenediamines in a molecular ratio of about 2:1, said reaction products containing compounds of the Formula (XVII):

$$R^1—C(O)—NH—R^2—N(R^3OH)—C(O)—R^1$$ Formula (XVII)

wherein R, $R^1$, $R^2$, and $R^3$ are defined as above; $A^-$ is as defined below.

In a yet further aspect, the fabric softening active may comprise the Formula (XVIII):

Formula (XVIII)

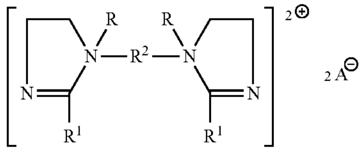

wherein R, $R^1$, $R^2$, and $R^3$ are defined as above; $A^-$ is as defined below.

In yet a further aspect, the fabric softening active may comprise the Formula (XIX);

Forumla (XIX)

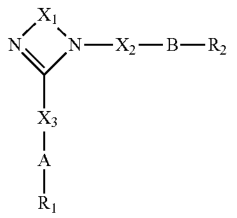

Wherein $X_1$ may comprise a $C_{2-3}$ alkyl group, in one aspect, an ethyl group; $X_2$ and $X_3$ may independently comprise $C_{1-6}$ linear or branched alkyl or alkenyl groups, in one aspect, methyl, ethyl or isopropyl groups; $R_1$ and $R_2$ may independently comprise $C_{8-22}$ linear or branched alkyl or alkenyl groups, characterized in that A and B are independently selected from the group comprising —O—(C═)—, —(C═O)—O—, or mixtures thereof, in one aspect, —O—(C═O)—.

Non-limiting examples of fabric softening actives comprising Formula (IX) are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate.

Non-limiting examples of fabric softening actives comprising Formula (XI) is 1,2 di (stearoyl-oxy) 3 trimethyl ammoniumpropane chloride.

Non-limiting examples of fabric softening actives comprising Formula (XII) may include dialkylenedimethylammonium salts such as dicanoladimethylammonium chloride, di(hard)tallowedimethylammonium chloride dicanoladimethylammonium methylsulfate. An example of commercially available dialkylenedimethylammonium salts usable in the present invention is dioleyldimethylammonium chloride available from Witco Corporation under the trade name Adogen® 472 and dihardtallow dimethylammonium chloride available from Akzo Nobel Arquad® 2HT75.

A non-limiting example of fabric softening actives comprising Formula (XIII) may include 1-methyl-1-stearoylamidoethyl-2-stearoylimidazolinium methylsulfate wherein $R^1$ is an acyclic aliphatic $C_{15}$-$C_{17}$ hydrocarbon group, $R^2$ is an ethylene group, G is a NH group, $R^5$ is a methyl group and $A^-$ is a methyl sulfate anion, available commercially from the Witco Corporation under the trade name Varisoft®.

A non-limiting example of fabric softening actives comprising Formula (XIV) is 1-tallowylamidoethyl-2-tallowylimidazoline wherein $R^1$ may comprise an acyclic aliphatic $C_{15}$-$C_{17}$ hydrocarbon group, $R^2$ may comprise an ethylene group, and G may comprise a NH group.

A non-limiting example of a fabric softening active comprising Formula (XV) is the reaction products of fatty acids with diethylenetriamine in a molecular ratio of about 2:1, said reaction product mixture comprising N,N"-dialkyldiethylenetriamine having the Formula (XX):

$R^1$—C(O)—NH—$CH_2CH_2$—NH—$CH_2CH_2$—NH—C(O)—$R^1$ Formula (XX)

wherein $R^1$ is an alkyl group of a commercially available fatty acid derived from a vegetable or animal source, such as Emersol® 223LL or Emersol® 7021, available from Henkel Corporation, and $R^2$ and $R^3$ are divalent ethylene groups.

A non-limiting example of a fabric softening active comprising Formula (XVI) is a difatty amidoamine based softener having the Formula (XXI):

[$R^1$—C(O)—NH—$CH_2CH_2$—N($CH_3$)($CH_2CH_2OH$)—$CH_2CH_2$—NH—C(O)—$R^1$]$^+$ $CH_3SO_4^-$ Formula (XXI)

wherein $R^1$ is an alkyl group. An example of such compound is that commercially available from the Witco Corporation e.g. under the trade name Varisoft® 222LT.

A non-limiting example of a fabric softening active comprising Formula (XVII) is the reaction products of fatty acids with N-2-hydroxyethylethylenediamine in a molecular ratio of about 2:1, said reaction product mixture comprising the Formula (XXII):

$R^1$—C(O)—NH—$CH_2CH_2$—N($CH_2CH_2OH$)—C(O)—$R^1$ Formula (XXII)

wherein $R^1$—C(O) is an alkyl group of a commercially available fatty acid derived from a vegetable or animal source, such as Emersol® 223LL or Emersol® 7021, available from Henkel Corporation.

A non-limiting example of a fabric softening active comprising Formula (XVIII) is the diquaternary compound having the Formula (XXIII):

Formula (XXIII)

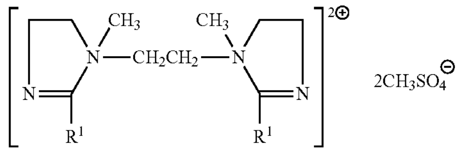

wherein $R^1$ is derived from fatty acid. Such compound is available from Witco Company.

A non-limiting example of a fabric softening active comprising Formula (XIX) is a dialkyl imidazoline diester compound, where the compound is the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid or a mixture of the above.

It will be understood that combinations of softener actives disclosed above are suitable for use herein.

Anion A

In the cationic nitrogenous salts herein, the anion $A^-$, which comprises any softener compatible anion, provides electrical neutrality. Most often, the anion used to provide electrical neutrality in these salts is from a strong acid, especially a halide, such as chloride, bromide, or iodide. However, other anions can be used, such as methylsulfate, ethylsulfate, acetate, formate, sulfate, carbonate, and the like. In one aspect, the anion A may comprise chloride or methylsulfate. The anion, in some aspects, may carry a double charge. In this aspect, $A^-$ represents half a group.

In one aspect, the fabric care and/or treatment composition may comprise a second softening agent selected from the group consisting of polyglycerol esters (PGEs), oily sugar derivatives, and wax emulsions. Suitable PGEs include those disclosed in U.S. PA 61/089,080. Suitable oily sugar derivatives and wax emulsions include those disclosed in USPA 2008-0234165 A1.

In one aspect, the compositions may comprise from about 0.001% to about 0.01% of an unsaturated aldehyde. In one aspect, the compositions are essentially free of an unsaturated aldehyde. Without being limited by theory, in this aspect, the compositions are less prone to the yellowing effect often encountered with amino-containing agents.

Builders—The compositions may also contain from about 0.1% to 80% by weight of a builder. Compositions in liquid form generally contain from about 1% to 10% by weight of the builder component. Compositions in granular form generally contain from about 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other suitable polycarboxylates for use herein are the polyacetal carboxylates described in U.S. Pat. No. 4,144,226 and U.S. Pat. No. 4,246,495. Other polycarboxylate builders are the oxydisuccinates and the ether carboxylate builder compositions comprising a combination of tartrate monosuccinate and tartrate disuccinate described in U.S. Pat. No. 4,663,071, Builders for use in liquid detergents are described in U.S. Pat. No. 4,284,532, One suitable builder includes may be citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites. Such materials and their use as detergent builders are more fully discussed in U.S. Pat. No. 4,605,509.

Dispersants—The compositions may contain from about 0.1%, to about 10%, by weight of dispersants Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives thereof such as those described in U.S. Pat. Nos. 4,597,898, 4,676,921, 4,891,160, 4,659,802 and 4,661,288.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5%. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents—The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant—The compositions may contain less than about 5%, or from about 0.01% to about 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners—The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-isulphonate, benzoylvalerolactam, dodecanoyloxybenzenesulphonate. Suitable bleach boosters include those described in U.S. Pat. No. 5,817,614. Other bleaching agents include metal complexes of transitional metals with ligands of defined stability constants. Such catalysts are disclosed in U.S. Pat. Nos. 4,430,243, 5,576,282, 5,597,936 and 5,595,967.

Stabilizer—The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' perfumes and/or perfume systems. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked. In one aspect, the organosilicones may be linear.

In one aspect, the organosilicone may comprise a non-functionalized siloxane polymer that may have Formula (XXIV) below, and may comprise polyalkyl and/or phenyl silicone fluids, resins and/or gums.

$$[R_1R_2R_3SiO_{1/2}]_n[R_4R_4SiO_{2/2}]_m[R_4SiO_{3/2}]_j \quad \text{Formula (XXIV)}$$

wherein:

i) each $R_1$, $R_2$, $R_3$ and $R_4$ may be independently selected from the group consisting of H, —OH, $C_1$-$C_{20}$ alkyl, $C_1$-$C_{20}$ substituted alkyl, $C_6$-$C_{20}$ aryl, $C_6$-$C_{20}$ substituted aryl, alkylaryl, and/or $C_1$-$C_{20}$ alkoxy, moieties;

ii) n may be an integer from about 2 to about 10, or from about 2 to about 6; or 2; such that n=j+2;

iii) m may be an integer from about 5 to about 8,000, from about 7 to about 8,000 or from about 15 to about 4,000;

iv) j may be an integer from 0 to about 10, or from 0 to about 4, or 0;

In one aspect, $R_2$, $R_3$ and $R_4$ may comprise methyl, ethyl, propyl, $C_4$-$C_{20}$ alkyl, and/or $C_6$-$C_{20}$ aryl moieties. In one aspect, each of $R_2$, $R_3$ and $R_4$ may be methyl. Each $R_1$ moiety blocking the ends of the silicone chain may comprise a moiety selected from the group consisting of hydrogen, methyl, methoxy, ethoxy, hydroxy, propoxy, and/or aryloxy.

As used herein, the nomenclature SiO"n"/2 represents the ratio of oxygen and silicon atoms. For example, $SiO_{1/2}$ means that one oxygen is shared between two Si atoms. Likewise $SiO_{2/2}$ means that two oxygen atoms are shared between two Si atoms and $SiO_{3/2}$ means that three oxygen atoms are shared are shared between two Si atoms.

In one aspect, the organosilicone may be polydimethylsiloxane, dimethicone, dimethiconol, dimethicone crosspolymer, phenyl trimethicone, alkyl dimethicone, lauryl dimethicone, stearyl dimethicone and phenyl dimethicone. Examples include those available under the names DC 200 Fluid, DC 1664, DC 349, DC 346G available from Dow Corning®Corporation, Midland, Mich., and those available under the trade names SF1202, SF1204, SF96, and Viscasil® available from Momentive Silicones, Waterford, N.Y.

In one aspect, the organo silicone may comprise a cyclic silicone. The cyclic silicone may comprise a cyclomethicone of the formula $[(CH_3)_2SiO]_n$ where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In one aspect, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. Such silicones are described in USPA 2005/0098759, and U.S. Pat. Nos. 4,818,421 and 3,299,112. Exemplary commercially available silicone polyethers include DC 190, DC 193, FF400, all available from Dow Corning® Corporation, and various Silwet® surfactants available from Momentive Silicones.

In another aspect, the functionalized siloxane polymer may comprise an aminosilicone. Suitable aminosilicones are described in U.S. Pat. Nos. 7,335,630 B2, 4,911,852, and USPA 2005/0170994A1. In one aspect the aminosilicone may be that described in U.S. PA 61/221,632. In another aspect, the aminosilicone may comprise the structure of Formula (XXV):

$$[R_1R_2R_3SiO_{1/2}]_n[(R_4Si(X{-}Z)O_{2/2}]_k[R_4R_4SiO_{2/2}]_m[R_4SiO_{3/2}]_j \quad \text{Formula (XXV)}$$

wherein i. $R_1$, $R_2$, $R_3$ and $R_4$ may each be independently selected from H, OH, $C_1$-$C_{20}$ alkyl, $C_1$-$C_{20}$ substituted alkyl, $C_6$-$C_{20}$ aryl, $C_6$-$C_{20}$ substituted aryl, alkylaryl, and/or $C_1$-$C_{20}$ alkoxy;

ii. Each X may be independently selected from a divalent alkylene radical comprising 2-12 carbon atoms, —$(CH_2)s$—wherein s may be an integer from about 2 to about 10; —$CH_2$—CH(OH)—$CH_2$—; and/or

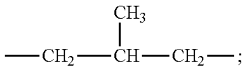

iii. Each Z may be independently selected from —$N(R_5)_2$;

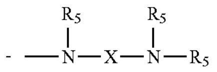 and 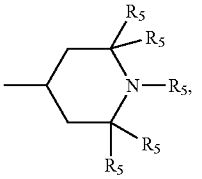

wherein each $R_5$ may be selected independently selected from H, $C_{20}$ alkyl; and $A^-$ may be a compatible anion. In one aspect, $A^-$ may be a halide;

iv. k may be an integer from about 3 to about 20, from about 5 to about 18 more or even from about 5 to about 10;

v. m may be an integer from about 100 to about 2,000, or from about 150 to about 1,000;

vi. n may be an integer from about 2 to about 10, or about 2 to about 6, or 2, such that n=j+2; and vii. j may be an integer from 0 to about 10, or from 0 to about 4, or 0;

In one aspect, $R_1$ may comprise —OH. In this aspect, the organosilicone is amidomethicone.

Exemplary commercially available aminosilicones include DC 8822, 2-8177, and DC-949, available from Dow Corning® Corporation, and KF-873, available from Shin-Etsu Silicones, Akron, Ohio.

In one aspect, the organosilicone may comprise amine ABn silicones and quat ABn silicones. Such organosilicones are generally produced by reacting a diamine with an epoxide. These are described, for example, in U.S. Pat. Nos. 6,903,061 B2, 5,981,681, 5,807,956, 6,903,061 and 7,273,837. These are commercially available under the trade names Magnasoft® Prime, Magnasoft® JSS, Silsoft® A-858 (all from Momentive Silicones).

In another aspect, the functionalized siloxane polymer may comprise silicone-urethanes, such as those described in U.S. PA 61/170,150. These are commercially available from Wacker Silicones under the trade name SLM-21200®.

When a sample of organosilicone is analyzed, it is recognized by the skilled artisan that such sample may have, on average, the non-integer indices for Formula (XXIV) and (XXV) above, but that such average indices values will be within the ranges of the indices for Formula (XXIV) and (XXV) above.

Perfume: The optional perfume component may comprise a component selected from the group consisting of (1) a perfume microcapsule, or a moisture-activated perfume microcapsule, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;

(2) a pro-perfume;

(3) a low odor detection threshold perfume ingredients, wherein said low odor detection threshold perfume ingredients may comprise less than about 25%, by weight of the total neat perfume composition; and (4) mixtures thereof; and The weight ratio of the fabric softening active to said carrier component may be from about 1:19 to about 19:1. In one aspect, the fabric conditioning composition exhibits a melting point greater than about 90° C.

Microcapsule—The compositions may comprise from about 0.05% to about 5%; or from about 0.1% to about 1% of a microcapsule. In one aspect, the microcapsule may comprise a shell comprising a polymer crosslinked with an aldehyde. In one aspect, the microcapsule may comprise a shell comprising a polymer selected from the group consisting of polyurea, polyurethane, polyamine, urea crosslinked with an aldehyde or melamine crosslinked with an aldehyde. Examples of materials suitable for making the shell of the microcapsule include melamine-formaldehyde, urea-formaldehyde, phenol-formaldehyde, or other condensation polymers with formaldehyde.

In one aspect, the microcapsules may vary in size (i.e., the maximum diameter is from about 1 to about 75 microns, or from about 5 to about 30 microns). The capsules may have an average shell thickness ranging from about 0.05 to about 10 microns, alternatively from about 0.05 to about 1 micron.

In one aspect, the microcapsule may comprise a perfume microcapsule. In turn, the perfume core may comprise a perfume and optionally a diluent. Suitable perfume microcapsules may include those described in the following references: published USPA Nos 2003-215417 A1; 2003-216488 A1; 2003-158344 A1; 2003-165692 A1; 2004-071742 A1; 2004-071746 A1; 2004-072719 A1; 2004-072720 A1; 2003-203829 A1; 2003-195133 A1; 2004-087477 A1; 2004-0106536 A1; U.S. Pat. Nos. 6,645,479; 6,200,949; 4,882,220; 4,917,920; 4,514,461; RE32713; 4,234,627; EP 1393706 A1. Capsules having a perfume loading of from about 50% to about 95% by weight of the capsule may be employed.

The shell material surrounding the core to form the microcapsule can be any suitable polymeric material which is impervious or substantially impervious to the materials in the core (generally a liquid core) and the materials which may come in contact with the outer surface of the shell. In one aspect, the material making the shell of the microcapsule may comprise formaldehyde. Formaldehyde based resins such as melamine-formaldehyde or urea-formaldehyde resins are especially attractive for perfume encapsulation due to their wide availability and reasonable cost.

One method for forming shell capsules useful herein is polycondensation, which may be used to produce aminoplast encapsulates. Aminoplast resins are the reaction products of one or more amines with one or more aldehydes, typically formaldehyde. Non-limiting examples of amines are melamine and its derivatives, urea, thiourea, benzoguanamine, and acetoguanamine and combinations of amines. Suitable cross-linking agents (e.g. toluene diisocyanate, divinyl benzene, butane diol diacrylate, etc) may also be used and secondary wall polymers may also be used as appropriate, as described in the art, e.g., anhydrides and their derivatives, particularly polymers and copolymers of maleic anhydride as disclosed in published USPA 2004-0087477 A1.

Microcapsules having the liquid cores and polymer shell walls as described above can be prepared by any conventional process which produces capsules of the requisite size, friability and water-insolubility. Generally, such methods as coacervation and interfacial polymerization can be employed in known manner to produce microcapsules of the desired characteristics. Such methods are described in Ida et al, U.S. Pat. Nos. 3,870,542; 3,415,758; and 3,041,288.

Cyclodextrin. A suitable moisture-activated perfume carrier that may be useful in the disclosed multiple use fabric conditioning composition may comprise cyclodextrin. As used herein, the term "cyclodextrin" includes any of the known cyclodextrins such as unsubstituted cyclodextrins containing from six to twelve glucose units, especially beta-cyclodextrin, gamma-cyclodextrin, alpha-cyclodextrin, and/or derivatives thereof, and/or mixtures thereof. A more detailed description of suitable cyclodextrins is provided in U.S. Pat. No. 5,714,137. Suitable cylodextrins herein include beta-cyclodextrin, gamma-cyclodextrin, alpha-cyclodextrin, substituted beta-cyclodextrins, and mixtures thereof. In one aspect, the cyclodextrin may comprise beta-cyclodextrin. Perfume molecules are encapsulated into the cavity of the cyclodextrin molecules to form molecular microcapsules, commonly referred to as cyclodextrin/perfume complexes. The perfume loading in a cyclodextrin/perfume complex may comprise from about 3% to about 20%, or from about 5% to about 18%, or from about 7% to about 16%, by weight of the cyclodextrin/perfume complex.

The cyclodextrin/perfume complexes hold the encapsulated perfume molecules tightly, so that they can prevent perfume diffusion and/or perfume loss, and thus reducing the odor intensity of the multiple use fabric conditioning composition. However, the cyclodextrin/perfume complex can readily release some perfume molecules in the presence of moisture, thus providing a long lasting perfume benefit. Non-limiting examples of preparation methods are given in U.S. Pat. Nos. 5,552,378, and 5,348,667.

Suitable cyclodextrin/perfume complexes (or perfume cyclodextrin microcapsule) may have a small particle size, typically from about 0.01 to about 200 micrometer, or from about 0.1 less than about 150 micrometer, or from about 1.0 to about 100 micrometer, or from about 10 to about 50 micrometer.

The multiple use fabric conditioning compositions may comprise of from about 0.1% to about 25%, or from about 1% to about 20%, or from about 3% to about 15%, or from about 5% to about 10%, by weight of the total fabric conditioning composition, of cyclodextrin/perfume complex.

Moisture-Activated Cellular Matrix Microcapsule Moisture-activated and/or water-soluble perfume cellular matrix microcapsules are solid particles containing perfume stably held in the cells within the particles. Details about moisture-activated perfume cellular matrix microcapsules are disclosed in U.S. Pat. No. 3,971,852. A suitable moisture-activated perfume cellular matrix microcapsule may be perfume starch microcapsule which uses starch as the cellular matrix material.

Moisture-activated perfume cellular matrix microcapsules may have a size of from about 0.5 micron to about 300 microns, from about 1 micron to about 200 microns, or from about 2 microns to about 100 microns. The perfume loading in the cellular matrix microcapsules may range from about 20% to about 70%, or from about 40% to about 60%, by weight of the microcapsules. Sufficient amount of perfume moisture-activated microcapsules should be used to deliver the desired levels of perfume, depending on the perfume loading of the microcapsules. For microcapsules with a perfume loading of about 50%, typical level of the matrix microcapsules may comprise from about 0.1% to about 15%, from about 0.5% to about 7%, from about 0.8% to about 8%, or from about 1% to about 6%, by weight of the multiple use fabric conditioning composition.

A dispersing agent may be used to distribute the moisture-activated perfume cellular matrix microcapsules uniformly in the molten multiple use fabric conditioning composition. Suitable dispersing agents for use in combination with moisture-activated cellular microcapsules include block copolymer having blocks of terephthalate and polyethylene oxide. More specifically, these polymers are comprised of repeating units of ethylene and/or propylene terephthalate and polyethylene oxide terephthalate at a molar ratio of poly(ethylene/propylene) terephthalate units to polyethylene oxide terephthalate units of from about 25:75 to about 35:65, said polyethylene oxide terephthalate containing polyethylene oxide blocks having molecular weights of from about 300 to about 2,000. The molecular weight of this polymeric dispersing agent may be in the range of from about 5,000 to about 55,000.

Another suitable dispersing agent for use in combination with moisture-activated cellular microcapsules may be block copolymer having blocks of polyethylene oxide and of polypropylene oxide. Non-limiting examples of dispersing agent of this type include Pluronic® surfactants and Tetronic® surfactants.

In the process of preparing a multiple use fabric conditioning bar, a suitable dispersing agent may first be added to the fabric conditioning composition melt mixture with mixing, and the moisture-activated perfume starch microcapsules may then be added to the melt mixture with mixing, and the resulting mixture may be poured into a mold to form a multiple use fabric conditioning bar.

Porous Carrier Microcapsule—A portion of the perfume composition can also be absorbed onto and/or into a porous carrier, such as zeolites or clays, to form perfume porous carrier microcapsules in order to reduce the amount of free perfume in the multiple use fabric conditioning composition. When the perfume is to be adsorbed onto zeolite, the perfume ingredients forming the encapsulated perfume composition can be selected according to the description provided in U.S. Pat. No. 5,955,419.

Pro-perfume—The perfume composition may additionally include a pro-perfume. Pro-perfumes may comprise nonvolatile materials that release or convert to a perfume material as a result of, e.g., simple hydrolysis, or may be pH-change-triggered pro-perfumes (e.g. triggered by a pH drop) or may be enzymatically releasable pro-perfumes, or light-triggered pro-perfumes. The pro-perfumes may exhibit varying release rates depending upon the pro-perfume chosen. Pro-perfumes suitable for use in the disclosed compositions are described in the following: U.S. Pat. Nos. 5,378,468; 5,626,852; 5,710,122; 5,716,918; 5,721,202; 5,744,435; 5,756,827; 5,830,835; and 5,919,752.

Processes of Making Fabric and/or Hard Surface Cleaning and/or Treatment Compositions The cleaning and/or treatment compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Method of Use

Certain of the consumer products disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

TEST METHODS

QCM-D Method for Measuring Fabric Deposition Kinetics of a Silicone Emulsion

Another aspect of the invention provides for methods of assessing the Tau Value of a silicone emulsion. Preferably the Tau Value is of about 10 or less, below 10, below 8, below 5 or even from below 5 to about 0.5.

This method describes the derivation of a deposition kinetics parameter (Tau) from deposition measurements made using a quartz crystal microbalance with dissipation measurements (QCM-D) with fluid handling provided by a high performance liquid chromatography (HPLC) pumping system. The mean Tau value is derived from duplicate runs, with each run consisting of measurements made using two flow cells in series.

QCM-D Instrument Configuration

A schematic of the combined QCM-D and pumping system is shown in FIG. 1.

Carrier Fluid Reservoirs:

Three one liter or greater carrier fluid reservoirs are utilized (15*a*, 15*b*, 15*c*) as follows:

Reservoir A: Deionized water (18.2 MΩ); Reservoir B: Hard water (15 mM $CaCl_2.2H_2O$ and 5 mM $MgCl_2.6H_2O$ in 18.2 MΩ water); and Reservoir C: Deionized water (18.2 MΩ). All reservoirs are maintained at ambient temperature (approximately 20° C. to 25° C.).

Fluids from these three reservoirs can be mixed in various concentrations under the control of a programmable HPLC pump controller to obtain desired water hardness, pH, ionic strength, or other characteristics of the sample. Reservoirs A and B are used to adjust the water hardness of the sample, and reservoir C is used to add the sample (16) to the fluid stream via the autosampler (17).

Carrier Fluid Degasser:

Prior to entering the pumps (18*a*, 18*b*, 18*c*), the carrier fluids must be degassed. This can be achieved using a 4-channel vacuum degasser (19) (a suitable unit is the Rheodyne/Systec® #0001-6501, Upchurch Scientific, a unit of IDEX® Corporation, 619 Oak Street, P.O. Box 1529 Oak Harbor, Wash. 98277). Alternatively, the carrier fluids can be degassed using alternative means such as degassing by vacuum filtration. The tubing used to connect the reservoirs to the vacuum degasser (20*a*, 20*b*, 20*c*) is approximately 1.60 mm nominal inside diameter (ID) PTFE tubing (for example, Kimble Chase Life Science and Research Products LLC 1022 Spruce Street PO Box 1502 Vineland N.J. 08362-1502, part number 420823-0018).

Pumping System:

Carrier fluid is pumped from the reservoirs using three single-piston pumps (18*a*, 18*b*, 18*c*), as typically used for HPLC (a suitable pump is the Varian ProStar 210 HPLC Solvent Delivery Modules with 5 ml pump heads, Varian Inc., 2700 Mitchell Drive, Walnut Creek Calif. 94598-1675 USA). It should be noted that peristaltic pumps or pumps equipped with a proportioning valve are not suitable for this method. The tubing (21*a*, 21*b*, 21*c*) used to connect the vacuum degasser to the pumps is the same dimensions and type as those connecting the reservoirs to the degassers.

Pump A is used to pump fluid from Reservoir A (deionized water). Additionally, Pump A is equipped with a pulse dampener (22) (a suitable unit is the 10 ml volume 60 MPa Varian part #0393552501, Varian Inc., 2700 Mitchell Drive, Walnut Creek Calif. 94598-1675 USA) through which the output of Pump A is fed.

Pump B is used to pump fluid from Reservoir B (hard water). The fluid outflow from Pump B is joined to the fluid outflow of Pump A using a T-connector (23). This fluid then passes through a backpressure device (24) that maintains at least approximately 6.89 MPa (a suitable unit is the Upchurch Scientific part number P-455, a unit of IDEX® Corporation, 619 Oak Street, P.O. Box 1529 Oak Harbor, Wash. 98277) and is subsequently delivered to a dynamic mixer (25).

Pump C is used to pump fluid from Reservoir C (deionized water). This fluid then passes through a backpressure device (26) that maintains at least approximately 6.89 MPa (a suitable unit is the Upchurch Scientific part number P-455, a unit of IDEX® Corporation, 619 Oak Street, P.O. Box 1529 Oak Harbor, Wash. 98277) prior to delivering fluid into the autosampler (17).

Autosampler:

Automated loading and injection of the test sample into the flow stream is accomplished by means of an autosampler device (17) equipped with a 10 ml, approximately 0.762 mm nominal ID sample loop (a suitable unit is the Varian ProStar 420 HPLC Autosampler using a 10 ml, approximately 0.762 mm nominal ID sample loop, Varian Inc., 2700 Mitchell Drive, Walnut Creek Calif. 94598-1675 USA). The tubing (27) used from the pump C outlet to the backpressure device (26), and from the backpressure device (26) to the autosampler (17) is approximately 0.254 mm nominal ID polyetheretherketone (PEEK™) tubing (suitable tubing can be obtained from Upchurch Scientific, a unit of IDEX Corporation, 619 Oak Street, P.O. Box 1529 Oak Harbor, Wash. 98277). Fluid exiting the autosampler is delivered to a dynamic mixer (25).

Dynamic Mixer:

All of the flow streams are combined in a 1.2 ml dynamic mixer (25) (a suitable unit is the Varian part #0393555001 (PEEK™), Varian Inc., 2700 Mitchell Drive, Walnut Creek Calif. 94598-1675 USA) prior to entering into the QCM-D instrument (28). The tubing used to connect pumps A & B (18*a*, 18*b*) to the dynamic mixer via the pulse dampener (22) and backpressure device (24) is the same dimensions and type as that connecting the pump C (18*c*) to the autosampler via the backpressure device (26). The fluid exiting the dynamic mixer passes through an approximately 0.138 MPa backpressure device (29) (a suitable unit is the Upchurch Scientific part number P-791, a unit of IDEX® Corporation, 619 Oak Street, P.O. Box 1529 Oak Harbor, Wash. 98277) before entering the QCM-D instrument.

QCM-D:

The QCM-D instrument should be capable of collecting frequency shift (Δf) and dissipation shift (ΔD) measurements relative to bulk fluid over time using at least two flow cells (29*a*, 29*b*) whose temperature is held constant at 25 C±0.3 C. The QCM-D instrument is equipped with two flow cells, each having approximately 140 μl in total internal fluid volume, arranged in series to enable two measurements (a suitable instrument is the Q-Sense E4 equipped with QFM 401 flow cells, Biolin Scientific Inc. 808 Landmark Drive, Suite 124 Glen Burnie, Md. 21061 USA). The theory and principles of the QCM-D instrument are described in U.S. Pat. No. 6,006,589. The tubing (30) used from the autosampler to the dynamic mixer and all device connections downstream thereafter is approximately 0.762 mm nominal ID PEEK™ tubing (Upchurch Scientific, a unit of IDEX® Corporation, 619 Oak Street, P.O. Box 1529 Oak Harbor, Wash. 98277). Total fluid volume between the autosampler (17) and the inlet to the first QCM-D flow cell (29*a*) is 3.4 ml±0.2 ml.

The tubing (32) between the first and second QCM-D flow cell in the QCM-D instrument should be approximately 0.762 mm nominal ID PEEK™ tubing (Upchurch Scientific, a unit of IDEX®Corporation, 619 Oak Street, P.O. Box 1529 Oak Harbor, Wash. 98277) and between 8 and 15 cm in length. The outlet of the second flow cell flows via PEEK™ tubing (30) 0.762 mm ID, into a waste container (31), which must reside between 45 cm and 60 cm above the QCM-D flow cell #2 (29*b*) surface. This provides a slight amount of backpressure, which is necessary for the QCM-D to maintain a stable baseline and prevent siphoning of fluid out of the QCM-D.

Test Sample Preparation

Silicone test materials are to be prepared for testing by being made into a simple emulsion of at least 0.1% test material concentration (wt/wt), in deionized water (i.e., not a complex formulation), with a particle size distribution which is stable for at least 48 hrs at room temperature. Those skilled in the art will understand that such suspensions can be produced using a variety of different surfactants or solvents, depending upon the characteristics of each specific material. Examples of surfactants & solvents which may be successfully used to create such suspensions include: ethanol, Isofol® 12, Arquad® HTL8-MS, Tergitol™ 15-S-5, Tergitol™ 15-S-12, Tergitol™ TMN-10 and Tergitol™ TMN-3. Salts or other chemical(s) that would affect the deposition of the active should not to be added to the test sample. Those skilled in the art will understand that such suspensions can be made by mixing the components together using a variety of mixing devices. Examples of suitable overhead mixers include: IKA® Labortechnik, and Janke & Kunkel IKA® WERK, equipped with impeller blade Divtech Equipment R1342. It is important that each test sample suspension has a volume-weighted, mode particle size of <1,000 nm and preferably >200 nm, as measured >12 hrs after emulsification, and <12 hrs prior to its use in the testing protocol. Particle size distribution is measured using a static laser diffraction instrument, operated in accordance with the manufactures instructions. Examples of suitable particle sizing instruments include: Horiba Laser Scattering Particle Size and Distributer Analyzer LA-930 and Malvern Mastersizer®.

The silicone emulsion samples, prepared as described above, are initially diluted to 2000 ppm (vol/vol) using degassed 18.2 MΩ water and placed into a 10 ml autosampler vial (Varian part RK60827510). The sample is subsequently diluted to 800 ppm with degassed, deionized water (18.2 MΩ) and then capped, crimped and thoroughly mixed on a Vortex mixer for 30 seconds.

QCM-D Data Acquisition

Microbalance sensors fabricated from AT-cut quartz and being approximately 14 mm in diameter with a fundamental resonant frequency of 4.95 MHz±50 KHz are used in this method. These microbalance sensors are coated with approximately 100 nm of gold followed by nominally 50 nm of silicon dioxide (a suitable sensor is available from Q-Sense®, Biolin Scientific Inc. 808 Landmark Drive, Suite 124 Glen Burnie, Md. 21061 USA). The microbalance sensors are loaded into the QCM-D flow cells, which are then placed into the QCM-D instrument. Using the programmable HPLC pump controller, the following three stage pumping protocol is programmed and implemented:

Fluid Flow Rates for Pumping Protocol:

Fluid flow rates for pumps are: Pump A: Deionized water (18.2 MΩ) at 0.6 ml/min; Pump B: Hard water (15 mM CaCl2.2H2O and 5 mM MgCl2.6H2O in 18.2 MΩ water) at 0.3 ml/min; and Pump C: Deionized water (18.2 MΩ) at 0.1 ml/min.

These flow rates are used throughout the three stages delineated below. The three stages described below are collectively referred to as the "pumping protocol". The test sample only passes over the microbalance sensor during Stage 2.

Pumping Protocol Stage 1: System Equilibration

Fluid flow using pumps A, B, and C is started and the system is allowed to equilibrate for at least 60 minutes at 25 C. Data collection using the QCM-D instrument should begin once fluid flow has begun. The QCM-D instrument is used to collect the frequency shift (Δf) and dissipation shift (ΔD) at the third, fifth, seventh, and ninth harmonics (i.e. f3, f5, f7, and f9 and d3, d5, d7, and d9 for the frequency and dissipation shifts, respectively) by collecting these measurements at each of these harmonics at least once every four seconds.

Stage 1 should be continued until stability is established. Stability is defined as obtaining an absolute value of less than 0.75 Hz/hour for the slope of the $1^{st}$ order linear best fit across 60 contiguous minutes of frequency shift and also an absolute value of less than 0.2 Hz/hour for the slope of the $1^{st}$ order linear best fit across 60 contiguous minutes of dissipation shift, from each of the third, fifth, seventh, and ninth harmonics. Meeting this requirement may require restarting this stage and/or replacement of the microbalance sensor.

Once stability has been established, the sample to be tested is placed into the appropriate position in the autosampler device for uptake into the sample loop. Six milliliters of the test sample is then loaded into the sample loop using the autosampler device without placing the sample loop in the path of the flow stream. The flow rate used to load the sample into the sample loop should be less than 0.5 ml/min to avoid cavitation.

Pumping Protocol Stage 2: Test Sample Analysis

At the beginning of this stage, the sample loop loaded with the sample is now placed into the flow stream of fluid flowing into the QCM-D instrument using the autosampler switching valve. This results in the dilution and flow of the test sample across the QCM-D sensor surfaces. Data collection using the QCM-D instrument should continue throughout this stage. The QCM-D instrument is used to collect the frequency shift (Δf) and dissipation shift (ΔD) at the third, fifth, seventh, and ninth harmonics (i.e. f3, f5, f7, and f9 and d3, d5, d7, and d9 for the frequency and dissipation shifts, respectively) by collecting these measurements at each of these harmonics at least once every four seconds. Flow of the test sample across the QCM-D sensor surfaces should proceed for 30 minutes before proceeding to Stage 3.

Pumping Protocol Stage 3: Rinsing

In Stage 3, the sample loop in the autosampler device is removed from the flow stream using the switching valve present in the autosampler device. Fluid flow is continued as described in Stage 1 without introducing any additional test sample. This fluid flow will rinse out residual test sample from the tubing, dynamic mixer, and QCM-D flow cells. Data collection using the QCM-D instrument should continue throughout this stage. The QCM-D instrument is used to collect the frequency shift (Δf) and dissipation shift (ΔD) at the third, fifth, seventh, and ninth harmonics (i.e. f3, f5, f7, and f9 and d3, d5, d7, and d9 for the frequency and dissipation shifts, respectively) by collecting these measurements at each of these harmonics at least once every four seconds. Flow of the rinsing solution across the QCM-D sensor surfaces should proceed for 20 minutes of rinsing before stopping the flow and QCM-D data collection. The residual sample is removed from the sample loop in the autosampler through the use of nine 10 ml rinse cycles of deionized (18 MΩ) water, each drained to waste.

Upon completion of the pumping protocol, the QCM-D flow cells should be removed from the QCM-D instrument, disassembled, and the microbalance sensors discarded. The metal components of the flow cell should be cleaned by soaking in HPLC grade methanol for one hour followed by subsequent rinses with methanol and HPLC grade acetone. The non-metal components should be rinsed with deionized water (18 MΩ). After rinsing, the flow cell components should be blown dry with compressed nitrogen gas. All components of the pumping system connected in the flowstream during Stage 2 should be thoroughly rinsed by pumping 1.5 ml/min of Pump B and 3.5 ml/min of Pump A through all components at a flow rate of 5 ml/min for 10 min.

Data Analysis

Voigt Viscoelastic Fitting of the QCM-D Frequency Shift and Dissipation Shift Data Analysis of the frequency shift (Δf) and dissipation shift (ΔD) data is performed using the Voigt viscoelastic model as described in M.V.Voinova, M.Rodahl, M.Jonson and B.Kasemo "Viscoelastic Acoustic Response of Layered Polymer Films at Fluid-Solid Interfaces: Continuum Mechanics Approach" Physica Scripta 59: 391-396 (1999). The Voigt viscoelastic model is included in the Q-Tools software (Q-Sense®, version 3.0.7.230 and earlier versions), but could be implemented in other software programs. The frequency shift (Δf) and dissipation shift (ΔD) for each monitored harmonic should be zeroed approximately 5 minutes prior to injection of the test sample (i.e. five minutes prior to the beginning of Stage 2 described above).

Fitting of the Δf and ΔD data using the Voigt viscoelastic model is performed using the third, fifth, seventh, and ninth harmonics (i.e. f3, f5, f7, and f9, and d3, d5, d7, and d9, for the frequency and dissipation shifts, respectively) collected during Stages 2 and 3 of the pumping protocol described above. Voigt model fitting is performed using descending incremental fitting, i.e. beginning from the end of Stage 3 and working backwards in time.

In the fitting of Δf and ΔD data obtained from QCM-D measurements, a number of parameters must be determined or assigned. The values used for these parameters may alter the output of the Voigt viscoelastic model, so these parameters are specified here to remove ambiguity. These parameters are classified into three groups: fixed parameters, statically fit parameters, and dynamically fit parameters. The fixed parameters are selected prior to the fitting of the data and do not change during the course of the data fitting. The fixed parameters used in this method are: the density of the carrier fluid used in the measurement (1000 kg/m$^3$); the viscosity of the carrier fluid used in the measurement (0.001 kg/m-s); and the density of the deposited material (1000 kg/m$^3$).

Statically and dynamically fit parameters are optimized over a search range to minimize the error between the measured and predicted frequency shift and dissipation shift values.

Statically fit parameters are fit using the first time point of the data to be fit (i.e. the last time point in Stage 2) and then maintained as constants for the remainder of the fit. The statically fit parameter in this method is the elastic shear modulus of the deposited layer which was bound between 1 Pa and 10000 Pa, inclusive.

Dynamically fit parameters are fit at each time point of the data to be fit. At the first time point to be fit, the optimum dynamic fit parameters are selected within the search range described below. At each subsequent time point to be fit, the fitting results from the prior time point are used as a starting point for localized optimization of the fit results for the current time point. The dynamically fit parameters in this method are: the viscosity of the deposited layer which was bound between 0.001 kg/m-s and 0.1 kg-m-s, inclusive; and the thickness of the deposited layer which was bound between 0.1 nm and 1000 nm, inclusive.

Derivation of Deposition Kinetics Parameter (Tau) from Fit QCM-D Data

Once the layer viscosity, layer thickness, and layer elastic shear modulus are determined from the frequency shift and dissipation shift data using the Voigt viscoelastic model, the deposition kinetics of the test sample can be determined. Determination of the deposition kinetics parameter (Tau) is performed by fitting an exponential function to the layer viscosity using the equation:

$$\text{Viscosity}(t) = \text{Amplitude}\left(1 - \exp\left(-\left(\frac{t - t_0}{Tau}\right)\right)\right) + \text{Offset} \qquad \text{Equation 1}$$

where viscosity, amplitude, and offset have units of kg/m-s and t, $t_0$, and Tau have units of minutes, and "exp" refers to the exponential function $e^x$. The initial time-point of this function ($t_0$) is determined by the time at which the test sample begins flowing across the QCM-D sensor surface, as determined by the absolute value of the frequency shift on the 3$^{rd}$ harmonic ($|\Delta f3|$) being greater than 2 Hz. Equation 1 should be used only on data which fall between $t_0$ and the end of stage 2. The amplitude of this function is determined by subtracting the minimum film viscosity determined from the Voigt viscoelastic model during stage 2 of the HPLC method from the maximum film viscosity determined from the Voigt viscoelastic model during stage 2 of the HPLC method. The offset of this function is the minimum layer viscosity determined from the Voigt viscoelastic model during stage 2 of the HPLC method. Tau is fit to minimize the sum of squared differences between the layer viscosity and the viscosity fit determined using Equation 1. Tau should be calculated to one decimal place. Fitted values for Tau determined from the two QCM-D flow cells in series should be averaged together to provide a single value for Tau for each run. Subsequently, Tau values from the duplicate runs should be averaged together to determine the mean Tau value for the test sample.

Quality Assurance

This sample should be analyzed to test and confirm proper functioning of the QCM-D instrument method. This test must be run successfully before valid data can be acquired.

Stability Test

The purpose of this test is to evaluate the stability of the QCM-D response (i.e. frequency shift and dissipation shift) throughout the pumping protocol described above. In this test, the sample injected during stage 2 of the pumping protocol described above should be degassed, deionized water (18.2 MΩ). Frequency shift and dissipation shift data for the third, fifth, seventh, and ninth harmonics (f3, f5, f7, and f9 and d3, d5, d7, and d9 for the frequency and dissipation shifts, respectively) are to be monitored. For the purposes of this stability test, stability is defined as obtaining an absolute value of less than 0.75 Hz/hour for the slope of the $1^{st}$ order linear best fit across 30 contiguous minutes of frequency shift and also an absolute value of less than 0.2 Hz/hour for the slope of the $1^{st}$ order linear best fit across 30 contiguous minutes of dissipation shift, from each of the third, fifth, seventh, and ninth harmonics. If this stability criterion is not met during this test, this indicates failure of the stability test and evaluation of the implementation of the experimental method is required before further testing. Valid data cannot be acquired unless this stability test is run successfully.

Results

The Tau Value is calculated for the emulsions made, in accordance with the Test Sample Preparation Section of this specification, from organosilicones in Examples 1, 2 and 4 below.

| Material | Tau Value |
|---|---|
| Example 1 | 1.5 |
| Example 2 | 6.6 |
| Example 4 | 9.2 |

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Examples 1-10 are examples of making the organo modified silicones of the present invention.

Example 1

50.0 g of hydroxyethyleneoxypropylmethylsiloxane-dimethylsiloxane copolymers 40 mole % carbinol (available from Gelest, Morristown, Pa. catalog number CMS-626) and 0.5 mL of tin (IV) chloride are combined and heated to 80° C. with stirring. 5.13 g of $C_{12}$-$C_{14}$ Alkyl Glycidyl Ether—AGE-1214 (available from P&G Chemicals under the trade name AGE-1214) is added dropwise over 15 min and the mixture is heated for 2 hr at 120° C. and then 16 hr at 60° C., after which 0.5 mL water is added. NMR indicates complete consumption of the glycidyl ether to yield a viscous liquid.

Example 2

50.0 g of Hydroxypropyleneoxypropylmethylsiloxane-dimethylsiloxane copolymer with 5 Mole % carbinol (available from Gelest, Morristown, Pa. catalogue number CMS-222) and 0.5 mL of tin (IV) chloride are combined and heated to 80° C. with stirring. 6.01 g of 1,2-Epoxyhexadecane (available from Aldrich Chemicals, Milwaukee, Wis.) is added dropwise over 15 min and the mixture is heated for 2 hr at 120° C. and then 16 hr at 60° C., after which 0.5 mL water is added. NMR indicates complete consumption of the glycidyl ether to yield a viscous liquid.

Example 3

5.0 g of dry poly(dimethylsiloxane), diglycidyl ether terminated with molecular weight, Mn 980 (available from Aldrich Chemicals, Milwaukee, Wis.) is added dropwise over 10 min to 35.7 g of dry poly(propylene glycol) of molecular weight Mn 3500 (available from Aldrich Chemicals) in the presence of 0.5 ml of tin(IV) chloride at 1:2 epoxide:hydroxyl stoichiometry in 500 ml of toluene at 80° C. After 16 h, the catalyst is quenched with 2 ml water and all solvents removed under reduced pressure with heat to yield a liquid which has a viscosity of 4300 cP.

Example 4

68.4 g of dry poly(dimethylsiloxane), diglycidyl ether terminated of molecular weight Mn 5000 (available from Gelest, Morristown, Pa. catalogue number DMS-E21) is added dropwise over 10 min to 8.7 g of dry poly(propylene glycol) molecular weight 725 (available from Aldrich Chemicals) in the presence of 0.5 mL of tin(IV) chloride in 300 ml of toluene at 80° C. After 16 h, the catalyst is quenched with 2 ml water and all solvents removed under reduced pressure, with heat, to yield a viscous liquid.

Example 5

20.0 g of dry epoxycyclohexylethylmethylsiloxane-dimethylsiloxane copolymers with 8-10% epoxy (available from Gelest, Morristown, Pa. catalogue number ECMS-924) in 200 ml of dry dichloromethane is added dropwise, at room temperature, over 15 min to 59.0 g dry Poly(propylene glycol) monobutyl ether of molecular weight Mn 2500 (available from Aldrich Chemicals, Milwaukee, Wis.) in 200 ml of dichloromethane in the presence catalytic amount (1.25 wt %) of boron trifluoride-diethyl etherate at 1:1.1 epoxide:hydroxyl stoichiometry. After 16 h at room temperature, the catalyst is quenched with 2 ml water and all solvents removed under reduced pressure with heat to yield a liquid.

Example 6

Dry poly(propylene glycol) monobutyl monoglycidyl ether of molecular weight 1100 dissolved in toluene is added dropwise over 15 min to dry Hydroxypropyleneoxypropylmethylsiloxane-dimethylsiloxane copolymer with 5 Mole % carbinol (available from Gelest, Morristown, Pa. catalogue number CMS-222) in the presence of a catalytic amount of tin(IV) chloride at 1:1 epoxide:hydroxyl stoichiometry in toluene at 80° C. After 16 h, the catalyst is quenched with 2 ml water and all solvents removed under reduced pressure with heat to yield a liquid.

Example 7

Dry $C_{12}$-$C_{14}$ Alkyl Glycidyl Ether—AGE-1214 (available from P&G Chemicals under the trade name AGE-1214) in toluene is added dropwise over 15 min to dry Hydroxyethyleneoxypropylmethylsiloxane-dimethylsiloxane copolymers 40 mole % carbinol (available from Gelest, Morristown, Pa. catalog number CMS-626) in the presence of a catalytic amount of tin (IV) chloride at 1:1 epoxide:hydroxyl stoichiometry in toluene at 80° C. After 16 h, the catalyst is quenched with 2 ml water and all solvents removed under reduced pressure with heat to yield a liquid.

Example 8

Dry 1,2-Epoxyhexadecane (available from Aldrich Chemicals, Milwaukee, Wis.) in toluene is added dropwise over 15 min to dry Hydroxypropyleneoxypropylmethylsiloxane-dimethylsiloxane copolymer with 5 Mole % carbinol (available from Gelest, Morristown, Pa. catalogue number CMS-222) in the presence of a catalytic amount of tin(IV) chloride at 1:1 epoxide:hydroxyl stoichiometry in toluene at 80° C. After 16 h, the catalyst is quenched with 2 ml water and all solvents removed under reduced pressure with heat to yield a liquid.

Example 9

5.0 g of dry poly(dimethylsiloxane), diglycidyl ether terminated with molecular weight, Mn 980 (available from Aldrich Chemicals, Milwaukee, Wis.) is added dropwise over 10 min to 35.7 g of dry poly(propylene glycol) of molecular weight Mn 3500 (available from Aldrich Chemicals) in the presence of 0.5 ml of tin(IV) chloride at 1:2 epoxide:hydroxyl stoichiometry in 500 ml of toluene at 80° C. After 16 h, the catalyst is quenched with 2 ml water and all solvents removed under reduced pressure with heat to yield a liquid which has a viscosity of 4300 cP.

Example 10

30.0 g of dry poly(dimethylsiloxane), diglycidyl ether terminated of molecular weight Mn 5000 (available from Gelest, Morristown, Pa. catalogue number DMS-E21) is added dropwise over 10 min to 8.7 g of dry poly(propylene glycol)molecular weight 725 (available from Aldrich Chemicals) in the presence of 0.5 mL of tin(IV) chloride at 1:2 epoxide:hydroxyl stoichiometry in 500 ml of toluene at 80° C. After 16 h, the catalyst is quenched with 2 ml water and all solvents removed under reduced pressure with heat to yield a liquid which has a viscosity of 2900 cP.

Example 11

Liquid Detergent Fabric Care Compositions: Liquid detergent fabric care composition 11A is made by mixing together the ingredients listed in the proportions shown and compositions 11B-11E are made by mixing together the ingredients listed in the proportions shown:

| Ingredient (wt %) | 11A | 11B | 11C | 11D | 11E |
|---|---|---|---|---|---|
| $C_{12}$-$C_{15}$ alkyl polyethoxylate (1.8) sulfate[1] | 20.1 | 16.6 | 14.7 | 13.9 | 8.2 |
| $C_{11.8}$ linear alkylbenzene sulfonc acid[2] | — | 4.9 | 4.3 | 4.1 | 8.2 |
| $C_{16}$-$C_{17}$ branched alkyl sulfate[1] | — | 2.0 | 1.8 | 1.6 | — |
| $C_{12}$ alkyl trimethyl ammonium chloride[4] | 2.0 | | — | — | — |
| $C_{12}$ alkyl dimethyl amine oxide[5] | | 0.7 | 0.6 | — | — |
| $C_{12}$-$C_{14}$ alcohol 9 ethoxylate[3] | 0.3 | 0.8 | 0.9 | 0.6 | 0.7 |
| $C_{15}$-$C_{16}$ branched alcohol-7 ethoxylate[1] | — | — | — | — | 4.6 |
| 1,2 Propane diol[6] | 4.5 | 4.0 | 3.9 | 3.1 | 2.3 |
| Ethanol | 3.4 | 2.3 | 2.0 | 1.9 | 1.2 |
| $C_{12}$-$C_{18}$ Fatty Acid[5] | 2.1 | 1.7 | 1.5 | 1.4 | 3.2 |
| Citric acid[7] | 3.4 | 3.2 | 3.5 | 2.7 | 3.9 |
| Protease[7] (32 g/L) | 0.42 | 1.3 | 0.07 | 0.5 | 1.12 |
| Fluorescent Whitening Agent[8] | 0.08 | 0.2 | 0.2 | 0.17 | 0.18 |
| Diethylenetriamine pentaacetic acid[6] | 0.5 | 0.3 | 0.3 | 0.3 | 0.2 |
| Ethoxylated polyamine[9] | 0.7 | 1.8 | 1.5 | 2.0 | 1.9 |
| Grease Cleaning Alkoxylated Polyalkylenimine Polymer[10] | — | — | 1.3 | 1.8 | — |
| Zwitterionic ethoxylated quaternized sulfated hexamethylene diamine[11] | — | 1.5 | — | — | 0.8 |
| Hydrogenated castor oil[12] | 0.2 | 0.2 | | 0.12 | 0.3 |
| Copolymer of acrylamide and methacrylamidopropyl trimethylammonium chloride[13] | 0.3 | 0.2 | 0.3 | 0.1 | 0.3 |
| Organosiloxane polymer of any of Examples 1-26 and 30-35 (mixtures thereof may also be used) | 6.0 | 6.0 | 3.0 | 0.5 | 3.0 |
| Water, perfumes, dyes, buffers, solvents and other optional components | to 100% pH 8.0-8.2 | to 100% pH 8.0-8.2 | to 100% pH 8.0-8.2 | to 100% pH 8.0-8.2 | to 100% pH 8.0-8.2 |

Example 12

Liquid or Gel Detergents: Liquid or gel detergent fabric care compositions are prepared by mixing the ingredients listed in the proportions shown:

| Ingredient (wt %) | 12A | 12B | 12C | 12D | 12E |
|---|---|---|---|---|---|
| $C_{12}$-$C_{15}$ alkyl polyethoxylate (3.0) sulfate[1] | 8.5 | 2.9 | 2.9 | 2.9 | 6.8 |

-continued

| Ingredient (wt %) | 12A | 12B | 12C | 12D | 12E |
|---|---|---|---|---|---|
| $C_{11.8}$ linear alkylbenzene sulfonic acid[2] | 11.4 | 8.2 | 8.2 | 8.2 | 1.2 |
| $C_{14}$-$C_{15}$ alkyl 7-ethoxylate[1] | — | 5.4 | 5.4 | 5.4 | 3.0 |
| $C_{12}$-$C_{14}$ alkyl 7-ethoxylate[3] | 7.6 | — | — | — | 1.0 |
| 1,2 Propane diol | 6.0 | 1.3 | 1.3 | 6.0 | 0.2 |
| Ethanol | — | 1.3 | 1.3 | — | 1.4 |
| Di Ethylene Glycol | 4.0 | — | — | — | — |
| Na Cumene Sulfonate | — | 1.0 | 1.0 | 0.9 | — |
| $C_{12}$-$C_{18}$ Fatty Acid[5] | 9.5 | 3.5 | 3.5 | 3.5 | 4.5 |
| Citric acid | 2.8 | 3.4 | 3.4 | 3.4 | 2.4 |
| Protease (40.6 mg/g/)[7] | 1.0 | 0.6 | 0.6 | 0.6 | 0.3 |
| Natalase 200L (29.26 mg/g)[14] | — | 0.1 | 0.1 | 0.1 | — |
| Termamyl Ultra (25.1 mg/g)[14] | 0.7 | 0.1 | 0.1 | 0.1 | 0.1 |
| Mannaway 25L (25 mg/g)[14] | 0.1 | 0.1 | 0.1 | 0.1 | 0.02 |
| Whitezyme (20 mg/g)[14] | 0.2 | 0.1 | 0.1 | 0.1 | — |
| Fluorescent Whitening Agent[8] | 0.2 | 0.1 | 0.1 | 0.1 | — |
| Diethylene Triamine Penta Methylene Phosphonic acid | — | 0.3 | 0.3 | 0.3 | 0.1 |
| Hydroxy Ethylidene 1,1 Di Phosphonic acid | 1.5 | — | — | — | — |
| Zwitterionic ethoxylated quaternized sulfated hexamethylene diamine[11] | 2.1 | 1.0 | 1.0 | 1.0 | 0.7 |
| Grease Cleaning Alkoxylated Polyalkylenimine Polymer[10] | — | 0.4 | 0.4 | 0.4 | — |
| PEG-PVAc Polymer[15] | 0.9 | 0.5 | 0.5 | 0.5 | — |
| Hydrogenated castor oil[12] | 0.8 | 0.4 | 0.4 | 0.4 | 0.3 |
| Terpolymer of acrylamide, acrylic acid and methacrylamidopropyl trimethylammonium chloride[13] | — | 0.2 | 0.2 | 0.2 | 0.2 |
| Borate | — | 1.3 | — | — | 1.2 |
| 4 Formyl Phenyl Boronic Acid | — | — | 0.025 | — | — |
| Organosiloxane polymer of Examples 1-26 and 30-35? | 3.0 | 4.5 | 2.0 | 3.0 | 4.5 |
| Water, perfumes, dyes, buffers, neutralizers, stabilizers and other optional components | to 100% pH 8.0-8.2 | to 100% pH 8.0-8.2 | to 100% pH 8.0-8.2 | to 100% pH 8.0-8.2 | to 100% pH 8.0-8.2 |

[1]Available from Shell Chemicals, Houston, TX.
[2]Available from Huntsman Chemicals, Salt Lake City, UT.
[3]Available from Sasol Chemicals, Johannesburg, South Africa
[4]Available from Evonik Corporation, Hopewell, VA.
[5]Available from The Procter & Gamble Company, Cincinnati, OH.
[6]Available from Sigma Aldrich chemicals, Milwaukee, WI
[7]Available from Genencor International, South San Francisco, CA.
[8]Available from Ciba Specialty Chemicals, High Point, NC
[9]600 g/mol molecular weight polyethylenimine core with 20 ethoxylate groups per —NH and available from BASF (Ludwigshafen, Germany)
[10]600 g/mol molecular weight polyethylenimine core with 24 ethoxylate groups per —NH and 16 propoxylate groups per —NH. Available from BASF (Ludwigshafen, Germany).
[11]Described in WO 01/05874 and available from BASF (Ludwigshafen, Germany)
[12]Available under the tradename ThixinR from Elementis Specialties, Highstown, NJ
[13]Available from Nalco Chemicals, Naperville, IL.
[14]Available from Novozymes, Copenhagen, Denmark.
[15]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany).

Example 13

Rinse-Added Fabric Care Compositions

Rinse-Added fabric care compositions are prepared by mixing together ingredients shown below:

| Ingredient | 13A | 13B | 13C | 13D |
|---|---|---|---|---|
| Fabric Softener Active[1] | 16.2 | 11.0 | 16.2 | — |
| Fabric Softener Active[2] | — | — | — | 5.0 |
| Cationic Starch[3] | 1.5 | — | 1.5 | — |
| Polyethylene imine[4] | 0.25 | 0.25 | — | — |
| Quaternized polyacrylamide[5] | — | | 0.25 | 0.25 |
| Calcium chloride | 0.15 | 0. | 0.15 | — |
| Ammonium chloride | 0.1 | 0.1 | 0.1 | — |

-continued

| Ingredient | 13A | 13B | 13C | 13D |
|---|---|---|---|---|
| Suds Suppressor[6] | — | — | — | 0.1 |
| Organosilicone of Examples 1-26 and 30-35 | 2.0 | 5.0 | 2.0 | 2.0 |
| Perfume | 0.85 | 2.0 | 0.85 | 1.0 |
| Perfume microcapsule[7] | 0.65 | 0.75 | 0.65 | 0.3 |
| Water, suds suppressor, stabilizers, pH control agents, buffers, dyes & other optional ingredients | to 100% pH = 3.0 | to 100% pH = 3.0 | to 100% pH = 3.0 | to 100% pH = 3.0 |

[1]N,N di(tallowoyloxyethyl)-N,N dimethylammonium chloride available from Evonik Corporation, Hopewell, VA.

[2]Reaction product of fatty acid with Methyldiethanolamine, quaternized with Methylchloride, resulting in a 2.5:1 molar mixture of N,N-di(tallowoyloxyethyl) N,N-dimethylammonium chloride and N-(tallowoyloxyethyl) N-hydroxyethyl N,N-dimethylammonium chloride available from Evonik Corporation, Hopewell, VA.

[3]Cationic starch based on common maize starch or potato starch, containing 25% to 95% amylose and a degree of substitution of from 0.02 to 0.09, and having a viscosity measured as Water Fluidity having a value from 50 to 84. Available from National Starch, Bridgewater, NJ

[4]Available from Nippon Shokubai Company, Tokyo, Japan under the trade name Epomin 1050.

[5]Cationic polyacrylamide polymer such as a copolymer of acrylamide/[2-(acryloylamino)ethyl]tri-methylammonium chloride (quaternized dimethyl aminoethyl acrylate) available from BASF, AG, Ludwigshafen under the trade name Sedipur 544.

[6]SILFOAM ® SE90 available from Wacker AG of Munich, Germany

[7]Available from Appleton Paper of Appleton, WI

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising, based on total composition weight:

a) from about 0.1% to about 50% of a surfactant selected from the group consisting of anionic, cationic, amphoteric, zwitterionic, nonionic surfactants, and combinations thereof; and b) from about 0.01% to about 20% of a random or blocky organosiloxane having the structure $$[R_1R_2R_3SiO_{1/2}]_{(j+2)}[(R_4Si(X\text{—}Z)O_{2/2}]_k[R_4R_4SiO_{2/2}]_m[R_4SiO_{3/2}]_j$$

wherein j is 0;

k is an integer from 0 to about 200;

m is an integer from 4 to about 5,000;

$R_1$, $R_2$ and $R_3$ are each $CH_3$ except when k=0, at least one of $R_1$, $R_2$ or $R_3$ is —X—Z;

each $R_4$ is $CH_3$;

each X is —$(CH_2)_s$—O— wherein each s independently is an integer from about 2 to about 8;

each Z is

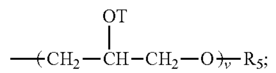

each $R_5$ is independently selected from the group consisting of $C_{12}$ alkyl, $C_5$-$C_{32}$ aryl, $C_5$-$C_{32}$ substituted aryl, $C_6$-$C_{32}$ alkylaryl, or $C_6$-$C_{32}$ substituted alkylaryl;

each T is H; and each v is an integer from 1 to about 10.

2. The composition according to claim 1 wherein k is an integer from 1 to about 50.

3. The composition according to claim 2 wherein said organosiloxane polymer has the structure:

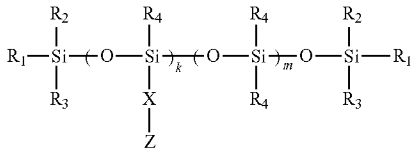

wherein m is an integer from about 10 to about 4000 and all other indices and moieties are as described in claim 2.

4. The composition of claim 1, said composition comprising a material selected from a perfume, a perfume delivery system, a brightener, an enzyme, a deposition aid, a structurant, a fabric softener active and mixtures thereof.

5. The composition according to claim 1 comprising an anionic surfactant.

6. The composition according to claim 5 wherein said anionic surfactant is selected from the group consisting of a $C_{11}$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, and mixtures thereof.

7. The composition of claim 4, wherein said fabric softener active is selected from the group consisting of polyglycerol esters, oily sugar derivatives, wax emulsions, N,N-bis (stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate and mixtures thereof.

8. The composition of claim 4, wherein said deposition aid polymer comprises a cationic polymer having a cationic charge from about 0.005 meq/g to about 23 meq/g at the pH of said composition.

9. A method of treating and/or cleaning a situs, said method comprising a.) optionally washing and/or rinsing said situs;

b.) contacting said situs with a composition according to claim 1 or claim 8; and c.) optionally washing and/or rinsing said situs.

10. The composition according to claim 1, wherein said organosiloxane polymer, when in the form of an emulsion, has a Tau Value of 10 or less.

11. The composition according to claim 1 wherein v is 1.

* * * * *